US006957187B1

(12) United States Patent
Kameda

(10) Patent No.: US 6,957,187 B1
(45) Date of Patent: Oct. 18, 2005

(54) SYSTEM FOR AIDING TO MAKE MEDICAL CARE SCHEDULE, AND PROGRAM STORAGE DEVICE READABLE BY THE SYSTEM

(75) Inventor: Toshitada Kameda, Kamogawa (JP)

(73) Assignee: Kameda Medical Information Laboratory, (JP)

( * ) Notice: Subject to any disclaimer, the term of this patent is extended or adjusted under 35 U.S.C. 154(b) by 0 days.

(21) Appl. No.: 09/330,094

(22) Filed: Jun. 11, 1999

(30) Foreign Application Priority Data

Jul. 27, 1998 (JP) ............................... P10-210496

(51) Int. Cl.$^7$ ............................................. G06F 17/60
(52) U.S. Cl. ............................................. 705/3; 705/2
(58) Field of Search ............................... 705/1, 2, 3–4; 600/300, 301

(56) References Cited

U.S. PATENT DOCUMENTS

| | | | |
|---|---|---|---|
| 5,065,315 A | 11/1991 | Garcia | |
| 5,072,383 A | 12/1991 | Brimm et al. | |
| 5,913,197 A | 6/1999 | Kameda | |
| 5,923,018 A | 7/1999 | Kameda et al. | |

FOREIGN PATENT DOCUMENTS

| | | |
|---|---|---|
| JP | 4-84945 | 3/1992 |
| JP | 8-266483 | 10/1996 |
| JP | 9-147027 | 6/1997 |
| JP | 9-185651 | 7/1997 |

*Primary Examiner*—Sam Rimell
(74) *Attorney, Agent, or Firm*—Finnegan, Henderson, Farabow, Garrett & Dunner, LLP

(57) ABSTRACT

A system for aiding to make a medical care schedule (1) is provided with a plurality of object files (21) respectively including (i) medical care data indicating either one of a plurality of types of medical care actions which are set in advance and (ii) setting order information to set at least relative execution timings as for the plurality of medical care actions, which compose one series of medical care schedule. The system is also provided with a process device (4) for setting, when the plurality of medical care actions composing one series of medical care schedule are designated, the at least relative execution timings of the designated plurality of medical care actions on a predetermined time axis, in accordance with the setting order information respectively included in the plurality of object files, which include the plurality of medical care data indicating the designated plurality of medical care actions. The system is further provided with a display device (5) for displaying a plurality of medical care data respectively indicating the plurality of medical care actions, the at least execution timings of which are set by the process device, in such a predetermined format that the medical care actions are respectively arranged in an order of the execution timings.

28 Claims, 20 Drawing Sheets

FIG. 2

| | 12-13-94 (Tues) 1st DAY (CCU) | 12-14-94 (Wed) 2nd DAY (CCU) | 12-15-94 (Thur) 3rd DAY (CCU) | | 12-19-94 (Mon) 7th DAY |
|---|---|---|---|---|---|
| RECORD | NURSING SCHEDULE | - - | | | - - |
| ACTIVITY RESTRICTION (REST/EXCRETION/CLEANNESS) | BED BATH PUDIC CLEAN WASH HELPER | BED BATH PUDIC CLEAN WASH HELPER | BED BATH | | BED BATH |
| MEAL | | MORNING : ○ LUNCH : △ DINNER : □ | | | ORDINARY MEAL |
| PRACTICE/MONITOR | VITAL SIGN WEIGHT MEASUREMENT SG CATHETER MONITOR CARDIOGRAM PULSE OXIMETER | VITAL SIGN WEIGHT MEASUREMENT | VITAL SIGN WEIGHT MEASUREMENT | | VITAL SIGN WEIGHT MEASUREMENT |
| TEST | CARDIOGRAM BREAST X RAY CPK, CPK-MB 24 hours FECALURIA | CARDIOGRAM BREAST X RAY CPK, CPK-MB 24 hours FECALURIA | CARDIOGRAM BREAST X RAY CPK, CPK-MB 24 hours FECALURIA | | CARDIOGRAM BREAST X RAY |
| ORAL MEDICINE/ EXTERNAL MEDICINE | | TIMELY ADMINISTRATION ⊕ | TIMELY ADMINISTRATION ⊕ | | TIMELY ADMINISTRATION ⊕ |
| INJECTION | INSTILLATION | INSTILLATION | INSTILLATION | | |
| TREATMENT | MT EVULSION S-G EVULSION DIV DELETION WPAPPING NEBLIZER SPIRON | A LINE EVULSION B CATH EVULSION NEBLIZER SPIRON | Y-DRAIN EVULSION NEBLIZER SPIRON | | NEBLIZER SPIRON |
| - - | | | | | |

◇ REST/EXCRETION/CLEANNESS
 ○ BED BATH

---

12-09-94 (Fri)　[HOSPITALIZATION 3rd DAY]

◇ DOCTOR'S RECORD
 ・OPERATION/SURGERY ORDER
◇ EVALUATION
 ○ VITAL SIGN
 ○ WEIGHT MEASUREMENT
◇ MEDICATION
 ○ 06:00　HEPARIN 3000 UNITS DIV
 ○ 12:00　HEPARIN 3000 UNITS DIV
 ○ 18:00　HEPARIN 3000 UNITS DIV
 ○ 24:00　HEPARIN 3000 UNITS DIV
 ○ TIMELY MEDICATION
　　: INDERAL TABLET 10mg 3TABLETS
　　　POSTCIBAL MORNING LUNCH DINNER (UNTIL12.12)
◇ TEST
 ◎ URINE GENERAL TEST
 ◎ URINE CHEMICAL TEST : CCr
 ◎ BLOOD SUGAR BURDEN TEST : TRETMENT
 ◎ 15:30　　CC-T
　　　　(RESERVATION AT HOSPITALIZATION)
 ◎ PM oncall　CAROTID ECHO
　　　　(RESERVATION AT HOSPITALIZATION)
◇ MEAL
 ○ MEAL INDICATION
　　: CARDIAC NORMAL FOOD 1600Cal NaCl5g
◇ REST/EXCRETION/CLEANNESS
 ○ SHOWER

---

12-10-94 (Sat)　[HOSPITALIZATION 4th DAY]

◇ DOCTOR'S RECORD
⋮

110

112

FIG.10
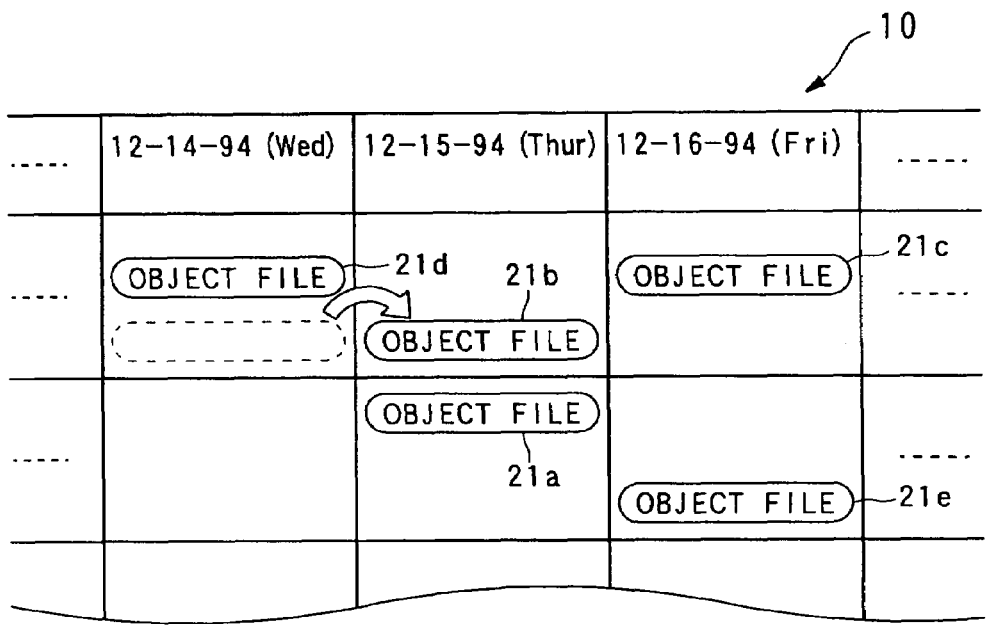
SET EXECUTION TIMINGS AGAIN
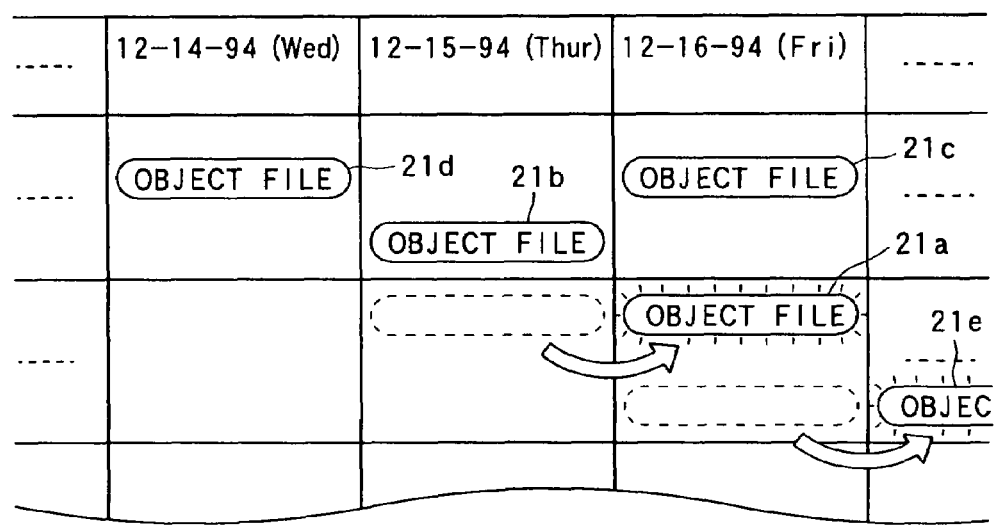

FIG.11

| | 12-07-94 (Wed) UPON HOSPITALIZING | 12-08-94 (Thur) 2nd DAY OF HOSPITALIZING |
|---|---|---|
| MEAL | CARDIAC NORMAL FOOD | CARDIAC NORMAL FOOD |
| TEST | 3 KINDS CULTURE | 9:00 CARDIOGRAM<br>10:00 BREAST X RAY<br>12:00 ANTIBODY TEST<br>15:00 IMA ECHO |

| | '95 March 2 MONTHS LEAVING HOSPITAL | '95 April 3 MONTHS LEAVING HOSPITAL | '95 May 4 MONTHS LEAVING HOSPITAL |
|---|---|---|---|
| MEDICATION | TIMELY MEDICATION | TIMELY MEDICATION | |
| TEST | March 4th CARDIOGRAM<br>March 18th CARDIOGRAM | April 15th CARDIOGRAM | May 15th CARDIOGRAM |

FIG. 18
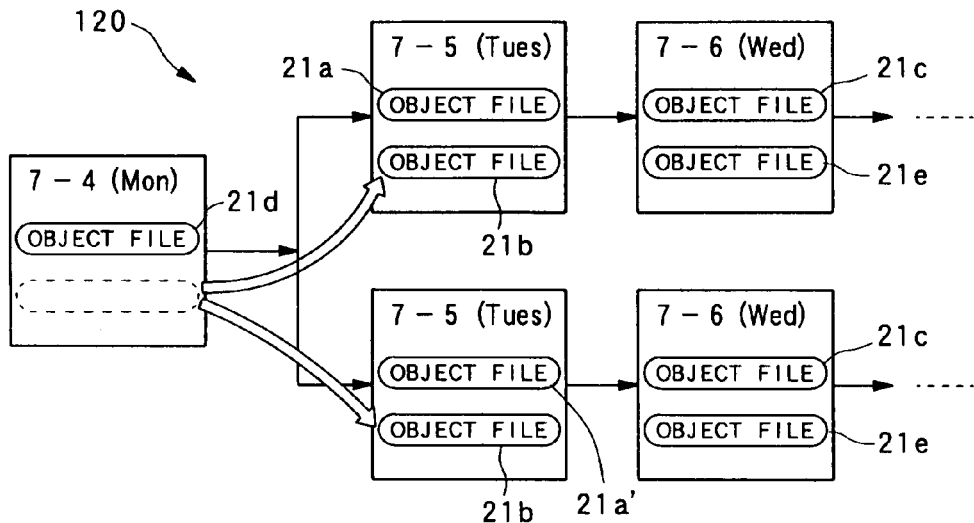
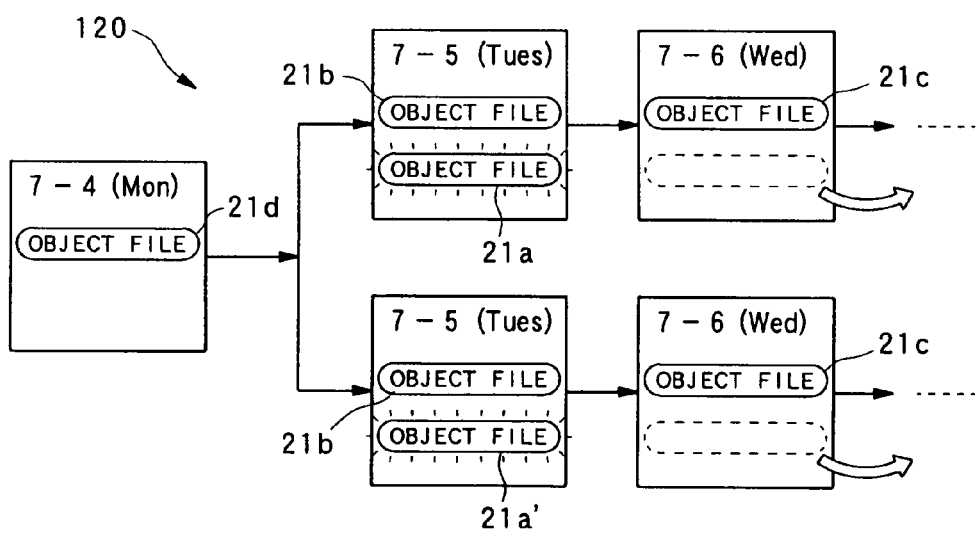

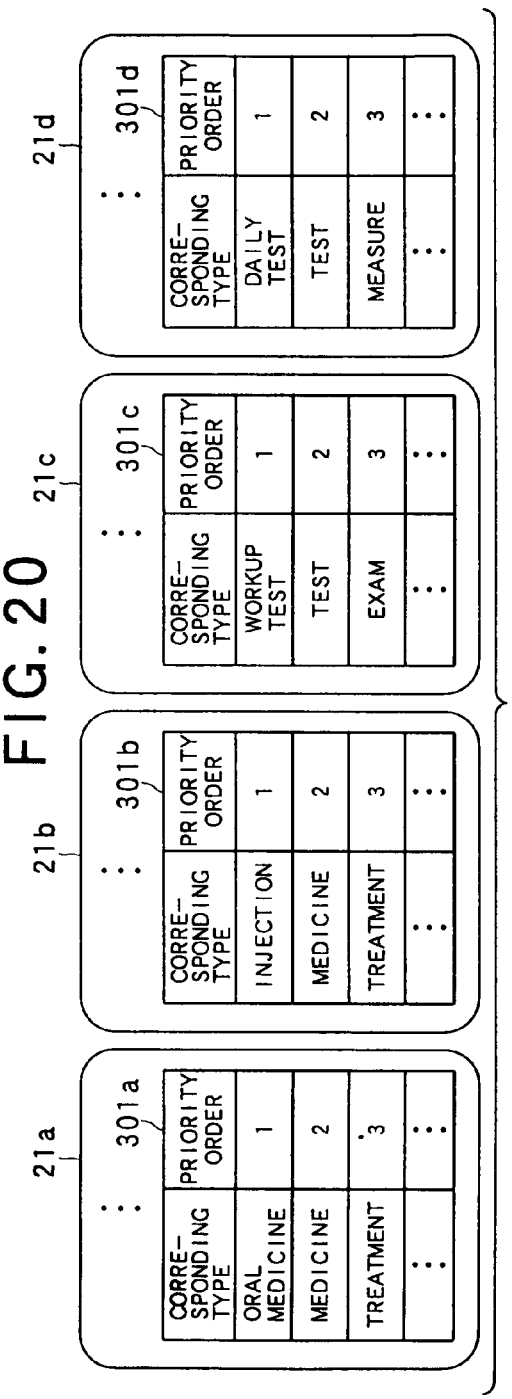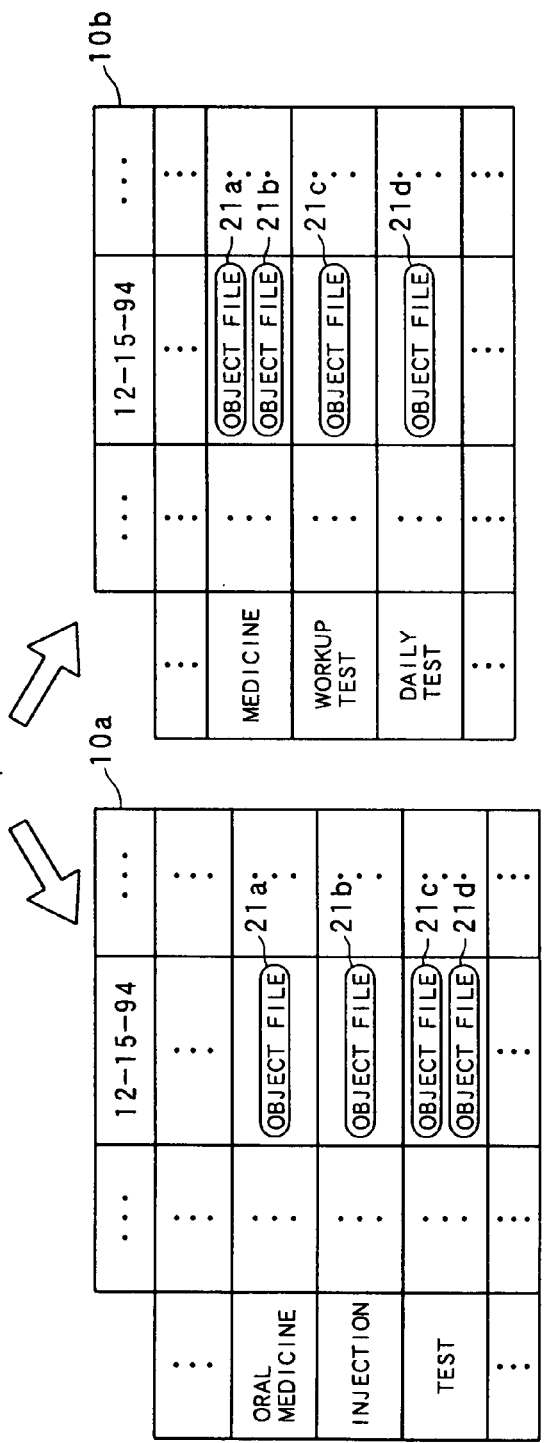
FIG. 20

FIG. 21

|  | ... | 12-13-94 | 12-14-94 | 12-15-94 |  | 12-19-94 |
|---|---|---|---|---|---|---|
| ⋮ | ⋮ | ⋮ | ⋮ | ⋮ |  | ⋮ |
| TEST | ⋮ | ◯◯ | ◯ | ◯ |  | ◯◯ | ← 21
| MEDICINE | ⋮ | ◯◯◯ | ◯◯◯ | ◯◯◯ |  | ◯◯◯ |
| INJECTION | ⋮ |  |  |  |  |  | } EMPTY
| MEAL | ⋮ | ◯ | ◯ | ◯ |  | ◯ | — 21
| REHABILI-TATION | ⋮ |  |  |  |  |  | } EMPTY
| ⋮ | ⋮ | ⋮ | ⋮ | ⋮ |  | ⋮ |

⬇ THIN OUT EMPTY ROW

|  | ... | 12-13-94 | 12-14-94 | 12-15-94 |  | 12-19-94 |
|---|---|---|---|---|---|---|
| ⋮ | ⋮ | ⋮ | ⋮ | ⋮ |  | ⋮ |
| TEST | ⋮ | ◯◯ | ◯ | ◯ |  | ◯◯ |
| MEDICINE | ⋮ | ◯◯◯ | ◯◯◯ | ◯◯◯ |  | ◯◯◯ |
| MEAL | ⋮ | ◯ | ◯ | ◯ |  | ◯ |
| ⋮ | ⋮ | ⋮ | ⋮ | ⋮ |  | ⋮ |

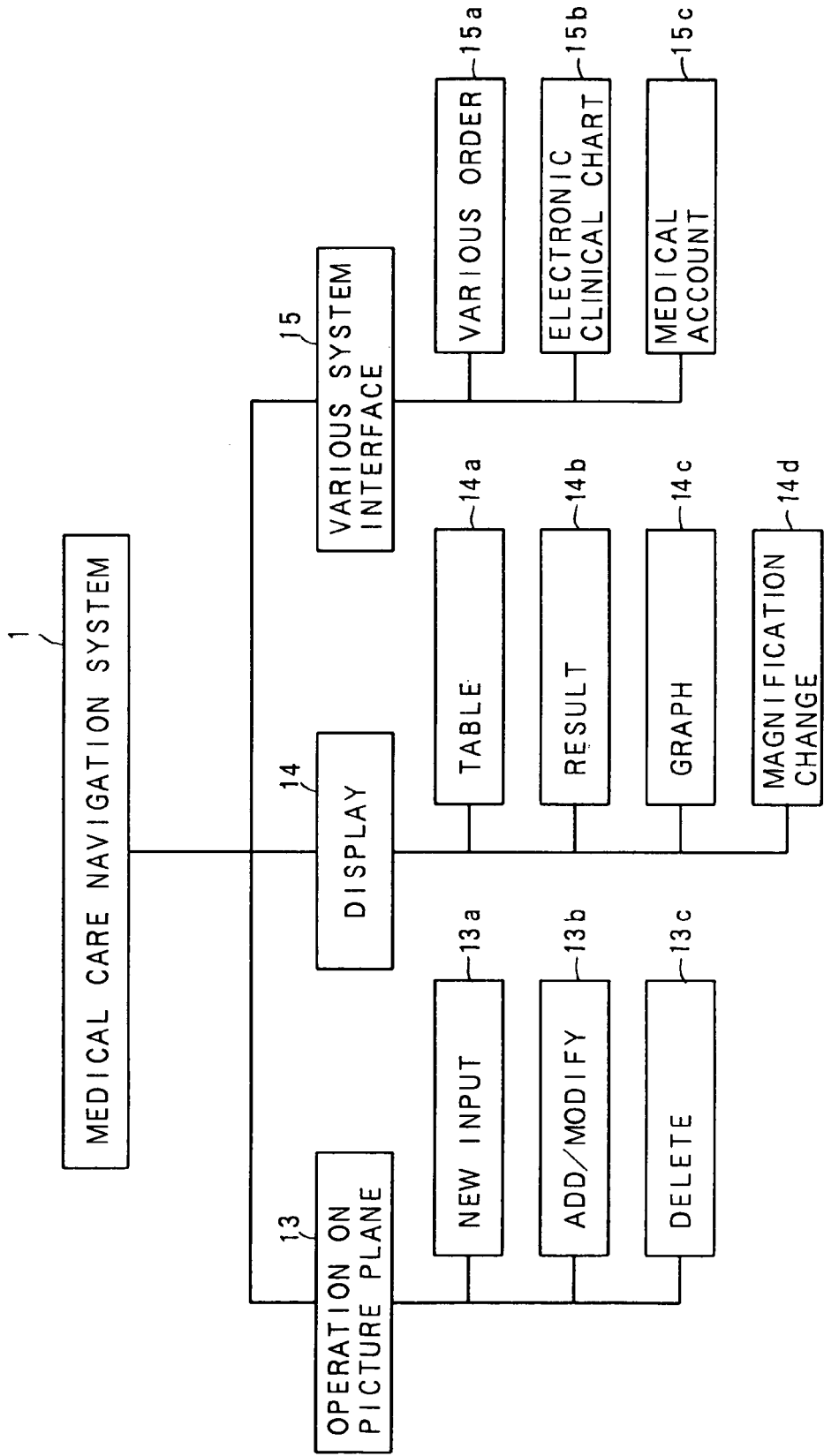

SYSTEM FOR AIDING TO MAKE MEDICAL CARE SCHEDULE, AND PROGRAM STORAGE DEVICE READABLE BY THE SYSTEM

BACKGROUND OF THE INVENTION

1. Field of the Invention

The present invention generally relates to a new system for aiding or navigating a person related to medical care such as a medical doctor, a nurse, a pharmacist, a medical office worker and so on, to make a medical care schedule. The present invention also relates to a computer readable program storage device for allowing a computer to function as the aiding system.

2. Description of the Related Art

Conventionally, in case that a certain patient comes to a hospital or is brought by an ambulance as an outpatient with a cardinal symptom (i.e., a cardinal symptom of sickness or illness) such as a headache, a sicchasia or vomiturition, a tinnitus, a stomachache and so on, the medical doctor performs an observation or examination for the patient. Then, at first the medical doctor makes up a medical care schedule in his or her mind as for a test, a medical service, an arrangement for hospitalization, a medical operation, an administration of medicine etc., after that in accordance with the observation and the diagnosis. Then, for example, the medical doctor may make such a schedule by writing, on a so-called "instruction table" sheet for exclusive use, the medical care schedule or plan for the patient such as the schedule and content of the test and the medication, the schedule and content of the medical operation, the schedule and content of the post-operation treatment or examination and so on.

Recently, as disclosed in Japanese Patent No. 2706645 (Japanese Patent Application Laying Open NO. Hei 9-185651) corresponding to U.S. patent application Ser. No. 08/746,175 which has been applied by the present inventor, it is also possible to make such a medical care schedule on a table, in which medical care actions of various types are arranged in first rows for each type of the medical care actions and in second rows orthogonal to the first rows for each date, displayed on a computer display. Namely, it is possible to make such a medical care schedule on a medical care schedule table which is displayed by executing a program called as a "care map" (which is a trade mark registered in Japan, and hereinbelow this kind of medical care schedule table is simply referred to as a "care map" as the occasion demands), by filling each item in the care map in accordance with the diagnosis or observation of the medical doctor. More concretely, the medical care schedule maker such as a medical care doctor sets medical care items related to the pertinent patient as the items to constitute the ordinate (first row) of the table and also sets an appropriate term assigned to the date constituting the abscissa (second row) of the table in which the medical care actions belonging to the set items will be performed, in accordance with the diagnosis or observation, so that the frames of the care map are constructed. Further, he or she inputs the medical care actions to be performed into each frame of the care map at the date and item corresponding thereto (hereinbelow, each frame of the table is called as a "cell" as the occasion demands). Then, after the scheduled medical care action is performed, a performance or result data remains as a confirmed data in each cell of the care map in place of the schedule data. Namely, in this care map, the schedule data is shown with the performance or result record data.

Especially, according to the above mentioned care map, since the hospital concerned personnel such as the medical doctor, the nurse, the pharmacist etc., who actually performs the medical care schedule share the medical care schedule information, it is possible to make the medical care schedule with little loss and perform the medical care schedule while appropriately adjusting or amending it in cooperation with each other e.g., inputting and changing the data associated with each cell (or each item) in the care map at each of the terminals.

However, according to the above mentioned care map, especially in a sophisticated actual medical field nowadays, since a large number of medical care actions and/or a large number of medical resources are inter-related to each other in a complicated manner, it is difficult for a person to appropriately or speedily make the medical care schedule, unless he or she is a veteran or old-professional person who knows mutual relationships between the medical care actions such as the nutrition restriction, the medical administration, the workup test, the diagnosis, the medical operation, the rehabilitation and so on (i.e., unless he or she knows when and what kinds of medical care actions should be performed, in order to perform one medical care action at a specific date or time, with respect to this specific date or time as a standard).

Furthermore, in case that the date when the workup examination as one of the medical care actions is changed or in case that a special workup examination is additionally performed which requires additional days, if the schedule date as for this specific item in the care map is changed, the date as for another item which is to be performed after this specific item such as a medical operation, the date as for another item which is to be performed before this specific item such as another workup examination, the date as for another item which is to be performed immediately before or after this specific item such as a nutrition restriction or medicine administration, should be also changed.

Namely, although the activity to input each item in the care map on the computer display is rather easy for the veteran or old-professional doctor or the like, it is very inconvenient since, when one portion of the medical care schedule consisting of a large number of items which have been once determined is to be changed, another item which is related to the changed one portion should be also inputted again, which is a problem. For example, in case that an emergent patient due to an traffic accident is received or a medical doctor cannot follow his schedule, by changing just the date for one item or by changing just the content of the medical care action such as the kind of the medicine rather slightly, the changes as for other large number of items become inevitable in actual cases, so that this problem is very serious. Especially, in a hospital where a large number of serious or urgent patients are accommodated, if such a job or activity to make the medical care schedule cannot be speedily performed, it may lead to a fatal event related to a human life. Thus, the veteran or old-professional doctor etc., should spend his or her time and energy in a large amount for the job or activity to change the medical care schedule itself, resulting in that the valuable medical resource runs short corresponding to that amount.

SUMMARY OF THE INVENTION

It is therefore an object of the present invention to provide a system for aiding to make a medical care schedule, which can aid or navigate the person who makes up the medical care schedule such as a medical doctor, a nurse, etc., to make an appropriate medical care schedule easily and speedily, and a program storage device, which allows a computer to function as the aiding system.

The above object of the present invention can be achieved by a first system for aiding to make a medical care schedule. The first system is provided with: a plurality of object files respectively including (i) medical care data indicating either one of a plurality of types of medical care actions which are set in advance and (ii) setting order information to set at least relative execution timings as for the plurality of medical care actions, which compose one series of medical care schedule; a process device for setting, when the plurality of medical care actions composing one series of medical care schedule are designated, the at least relative execution timings of the designated plurality of medical care actions on a predetermined time axis, in accordance with the setting order information respectively included in the plurality of object files, which include the plurality of medical care data indicating the designated plurality of medical care actions; and a display device for displaying a plurality of medical care data respectively indicating the plurality of medical care actions, the at least execution timings of which are set by the process device, in such a predetermined format that the medical care actions are respectively arranged in an order of the execution timings.

According to the first system, each of the object files includes the medical care data and the setting order information. When making the medical care schedule, the medical care actions composing one series of medical care schedule are designated one by one by an inputting operation through an input device such as a key board, a mouse or the like, by a medical care schedule maker such as a medical doctor, or are designated collectively in correspondence with a disease name, a patient attribute etc., by an inputting operation through a memory device such as a hard disc, a floppy disc or the like. Then, the at least relative execution timings as for the designated medical care actions are set by the process device such as a CPU (Central Processing Unit) or the like, on the predetermined time axis, in accordance with the setting order information respectively included in the plurality of object files. Here, "at least relative execution timings" may mean a concrete or absolute date e.g., X year, Y month, Z date when a pertinent medical care action is executed or just a relative date before or after a certain date as a reference such as a hospitalization date, a medical operation date or the like. When the execution timings are set in this manner, the plurality of medical care data respectively indicating the medical care actions, the execution timings of which are set, are displayed in such a predetermined format that the medical care actions are respectively arranged in the order of the execution timings such as a schedule table, a schedule list or the like.

In this way, as the medical care schedule maker such as a medical doctor performs an operation for designating the plurality of medical care actions composing one series of medical care schedule without designating the execution timings thereof, the at least relative execution timings thereof are automatically set in accordance with the setting order information included in the object files respectively, and the medical care data are displayed in the predetermined format on the basis of those automatically set execution timings. Thus, even in case that a plurality or a large number of medical care actions, which are complicatedly interrelated with each other, compose one series of medical care schedule, the medical care schedule in which the before and after relations and the relationships on the time axis between the plurality or the large number of medical care actions are appropriately prescribed, can be made easily and speedily. Therefore, since a knowledge as for the execution timings is not required for the medical care schedule maker, it is possible for an unskilled medical care schedule maker to easily and speedily make an appropriate medical care schedule, which is very convenient. Further, in case that the plurality of medical care actions are newly designated by adding, changing and/or erasing the medical care actions with respect to the plurality of medical care actions composing one series of medical care schedule which has been once made, the execution timings of the respective medical care actions are automatically set in accordance with the setting order information included in the object files. Therefore, it is not necessary for the medical care schedule maker to perform such a troublesome and time-consuming operation of shifting the execution timings of the respective medical care actions one by one, which is also very convenient.

In one aspect of the first system, the system is further provided with an input device for designating, as the plurality of medical care actions composing one series of medical care schedule, medical care actions scheduled to be performed in a future for a virtual patient, who has a specific disease, or a specific patient.

According to this aspect, when making the medical care schedule, the medical care actions scheduled to be performed in the future for a virtual patient, who has a specific disease, or a specific patient are designated as the plurality of medical care actions composing one series of medical care schedule, by the medical care schedule maker such as a medical doctor. Therefore, it is possible to make a substantially optimum medical care schedule for the virtual patient who has the specific disease or the specific patient.

In this aspect, the input device may be adapted to change at least partially the medical care actions and/or the execution timings in a condition where the medical care data are displayed in the predetermined format by the display device, the process device may set again the execution timings of the respective medical care actions after being changed by the input device in accordance with the setting order information, and the display device may display the medical care data indicating the respective medical care actions after being changed, in the predetermined format.

According to this aspect, while the medical care data are displayed in the predetermined format by the display device, the medical care actions and/or the execution timings are at least partially changed by the inputting device. Then, the execution timings of the respective medical care actions after being changed by the input device are set again by the process device, in accordance with the setting order information. Then, the medical care data indicating the respective medical care actions after being changed are displayed in the predetermined format by the display device. Therefore, in case that a change is applied to the plurality of medical care actions composing one series of medical care schedule which has been once made, the execution timings of not only the directly changed medical care action but also another medical care action to which a necessity of changing the execution timing is raised in correspondence with the change are automatically set in accordance with the setting order information included in the object files. Therefore, when the medical care schedule is partially changed, it is not necessary for the medical care schedule maker to perform such a troublesome and time-consuming operation of shifting the execution timings of the respective medical care actions, which have been once set, one by one.

In another aspect of the first system, the process device generates execution timing data indicating the set execution timings with respect to the object files respectively, the object files respectively store the generated execution timing data, and the display device displays the medical care data in the predetermined format, on the basis of the execution timings indicated by the stored execution timing data in addition to or in place of the set execution timings.

According to this aspect, the execution timing data indicating the set execution timings are generated by the process device with respect to the object files respectively and stored therein. Then, the medical care data are displayed by the display device in the predetermined format on the basis of the execution timings indicated by the stored execution timing data in addition to or in place of the set execution timings. Therefore, by performing the operation of setting the execution timings just once, as long as the medical care schedule is not changed, the medical care data can be displayed by the display device in the predetermined format on the basis of the execution timing data stored in the object files as they are. Further, upon changing the medical care schedule, the medical care data can be displayed by the display device in the predetermined format on the basis of the execution timing data, which are stored in the object file and which have been once set by a previous setting operation. Furthermore, it is also easy to apply a change to the medical care schedule, which has been once made, on this display picture plane.

In this aspect, the system may be further provided with a memory device for storing a data set, which includes a plurality of object files including a plurality of medical care data indicating a plurality of medical care actions composing one series of medical care schedule, in correlation with a patient code, which is uniquely assigned to each individual patient, wherein the input device may be adapted to designate the data set corresponding to the patient cord by designating the patient code, and the display device may display the medical care data in the predetermined format, on the basis of the execution timing data and the medical care data included in the designated data set.

According to this aspect, a data set, which includes the object files including the medical care data indicating the medical care actions composing one series of medical care schedule, are stored in the memory device, in correlation with the patient code. Later, the data set corresponding to the patient cord is designated by the input device, by designating the patient code. Then, the medical care data are displayed by the display device in the predetermined format, on the basis of the execution timing data and the medical care data included in the data set designated in this manner. Therefore, by making the medical care schedule once for an arbitrary patient, i.e., by designating the medical care actions and the execution timings thereof for him or her, it is possible to easily and speedily display the medical care schedule for the pertinent patient by reading out the medical care data from the memory device by designating the patient code assigned to the pertinent patient. Consequently, it is also possible to speedily apply the change to the medical care schedule.

In another aspect of the first system, in case that a plurality of medical care action candidates, one of which is to be disjunctively executed in a future, are designated in addition to or in place of the medical care action scheduled to be executed in the future, the process device sets at least relative execution timing candidates of the designated plurality of medical care action candidates in addition to or in place of the execution timing, in accordance with the setting order information, and the display device displays the medical care data respectively indicating the plurality of medical care action candidates in addition to or in place of the medical care data indicating the medical care action, in the predetermined format on the basis of the set execution timing candidates.

According to this aspect, the medical care action candidates, one of which is to be disjunctively executed in a future, are designated in addition to or in place of the medical care action scheduled to be executed in the future. Then, at least relative execution timing candidates of the designated plurality of medical care action candidates are set by the process device, in addition to or in place of the execution timing, in accordance with the setting order information. Then, on the basis of the set execution timing candidates, the medical care data respectively indicating the plurality of medical care action candidates in addition to or in place of the medical care data indicating the medical care action are displayed by the display device in the predetermined format. Therefore, in such a case that there are various medical care actions which have probabilities to be executed in the future in accordance with the disease, since the disease, the pathology etc., of the pertinent patient are not known at an initial stage of the medical care schedule e.g., before the diagnosis is not confirmed, this aspect of the present invention is very convenient for making the medical care schedule.

The object of the present invention can be also achieved by a second system for aiding to make a medical care schedule. The second system is provided with: a plurality of object files respectively including (i) medical care data indicating either one of a plurality of types of medical care actions which are set in advance, (ii) setting order information to set at least relative execution timings as for the plurality of medical care actions, which compose one series of medical care schedule and (iii) execution timing data indicating at least relative execution timings of respective one of the medical care actions indicated by the medical care data on a predetermined time axis; a display device for displaying a plurality of medical care data respectively indicating the plurality of medical care actions, the at least execution timings of which are set, in such a predetermined format that the medical care actions are respectively arranged in an order of the execution timings, on the basis of the execution timings indicated by the stored execution timing data; an input device for changing at least partially the medical care actions and/or the execution timings in a condition where the medical care data are displayed in the predetermined format by the display device; and a process device for setting the execution timings of the respective medical care actions after being changed by the input device in accordance with the setting order information included in the object files, which include the medical care data indicating the respective medical care actions after being changed by the input device, the display device displaying the medical care data indicating the respective medical care actions after being changed in the predetermined format, on the basis of the execution timings set by the process device.

According to the second system, each of the object files includes the medical care data, the setting order information and the execution timing data indicating at least relative execution timings of respective one of the medical care actions indicated by the medical care data on a predetermined time axis. On the basis of the execution timings indicated by the stored execution timing data, the medical care data are displayed by the display device in the predetermined format. Therefore, when making the medical care schedule, it is at first possible to display a standard or institutional medical care schedule, which is prepared in advance in correspondence with a disease name, a patient attribute etc., for example. In such a condition where the medical care data are displayed in the predetermined format, the medical care actions and/or the execution timings are at least partially changed by the input device. Then, the execution timings of the respective medical care actions after being changed are set by the process device such as a CPU etc., in accordance with the setting order information. Then, the medical care data indicating the respective medical care actions after being changed are displayed by the display device in the predetermined format. Therefore, in case of performing any change including an addition, an erase etc., with respect to the plurality of medical care actions composing one standard or institutional medical care schedule, which is prepared in advance, the execution timings of the respective medical care actions are automatically set in accordance with the setting order information included in the object files. Accordingly, it is possible for the medical care schedule maker to make an individual or exclusive medical care schedule for a specific patient by adding more or less change to the standard medical care schedule prepared in advance for each disease name, each patient attribute or the like as an original source. Moreover, since it is not necessary for the medical care schedule maker to perform such a troublesome and time-consuming operation of shifting the execution timings of the displayed medical care actions one by one, it is possible to easily and speedily make an appropriate medical care schedule.

In one aspect of the second system, the input device is adapted to designate a data set, which includes a plurality of object files including a plurality of medical care data indicating a plurality of medical care actions composing one series of medical care schedule, and the display device displays a plurality of the medical care data included in the designated data set, in the predetermined format on the basis of a plurality of the execution timing data included in the designated data set.

According to this aspect, a data set, which includes the object files including the medical care data indicating the medical care actions composing one series of medical care schedule, is designated by the input device. Then, the medical care data included in the designated data set are displayed by the display device in the predetermined format on the basis of the execution timing data included in the designated data set. Therefore, it is possible to speedily display a standard or institutional medical care schedule, which is prepared for each disease name, each patient attribute or the like for example.

In this aspect, a disease code, which is uniquely assigned to an individual disease in a plurality of types of diseases set in advance, may be respectively given to the data set, and the input device may be adapted to designate the data set corresponding to the disease cord by designating the disease code.

According to this aspect, a disease code is respectively given to the data set. Then, by designating the disease code through the input device, the data set corresponding to this disease code is designated. Then, the medical care data included in the object files included in the designated data set are displayed by the display device in the predetermined format. Therefore, since it is possible to at first speedily display a standard or institutional medical care schedule corresponding to a disease (e.g., myocrdial infrction, pneumonia, gastral cancer, cerebral infarction) for a patient upon making the medical care schedule for the patient, it is possible to efficiently start and perform a schedule making operation on the basis of this standard medical care schedule as an original source therefor.

Alternatively in this aspect, a patient attribute code, which is uniquely assigned to an individual patient attribute in a plurality of types of patient attributes including at least cardinal symptom and set in advance, may be respectively given to the data set, and the input device may be adapted to designate the data set corresponding to the patient attribute cord by designating the patient disease code.

According to this aspect, a patient attribute code is respectively given to the data set. Then, by designating the patient attribute code through the input device, the data set corresponding to this patient attribute code is designated. Then, the medical care data included in the object files included in the designated data set are displayed by the display device in the predetermined format. Therefore, since it is possible to at first speedily display a standard or institutional medical care schedule corresponding to a patient attribute (e.g., other than the cardinal symptom, sex, age, body complexion, vital sign and so forth) for a patient upon making the medical care schedule for the patient, it is possible to efficiently start and perform a schedule making operation on the basis of this standard medical care schedule as an original source therefor.

Further alternatively in this aspect, a patient code, which is uniquely assigned to an individual patient, may be respectively given to the data set, and the input device may be adapted to designate the data set corresponding to the patient cord by designating the patient code.

According to this aspect, a patient code is respectively given to the data set. Then, by designating the patient code through the input device, the data set corresponding to this patient code is designated. Then, the medical care data included in the object files included in the designated data set are displayed by the display device in the predetermined format. Therefore, since it is possible to at first speedily display a medical care schedule, which has been made for the pertinent patient or which has been performed for another patient who is similar to the pertinent patient upon making the medical care schedule for the patient, it is possible to efficiently start and perform a schedule making operation on the basis of this medical care schedule as an original source therefor.

In another aspect of the second system, the object files respectively include setting order information to set at least relative execution timing candidates as for a plurality of medical care action candidates, one of which is to be disjunctively executed in a future, in place of or in addition to the execution timings; the object files respectively store execution timing candidate data indicating the execution timing candidates in place of or in addition to the execution timing data; the display device displays a plurality of medical care data respectively indicating the plurality of medical care action candidates, in the predetermined format in place of or in addition to the medical care data respectively indicating the plurality of medical care actions; the input device is adapted to change the medical care action candidates and the execution timing candidates in place of or in addition to the medical care actions and the execution timings, in a condition where the medical care data are displayed in the predetermined format by the display device; the process device sets the execution timing candidates of the respective medical care action candidates after being changed by the input device, in place of or in addition to the execution timings, in accordance with the setting order information included in the object files, which include the medical care data indicating the respective medical care action candidates after being changed by the input device; and the display device displays the medical care data indicating the respective medical care action candidates after being changed, in place of or in addition to the medical care data indicating the respective medical care actions, in the predetermined format.

According to this aspect, the execution timing candidate data indicating the execution timing candidates are stored in the object file in place of or in addition to the execution timing data. Then, the medical care data respectively indicating the medical care action candidates are displayed by the display device in the predetermined format in place of or in addition to the medical care data respectively indicating the medical care actions. In a condition where the medical care data are displayed in the predetermined format in this manner, the medical care action candidates and the execution timing candidates are changed by the input device, in place of or in addition to the medical care actions and the execution timings. Then, the execution timing candidates of the respective medical care action candidates after being changed are set by the process device, in place of or in addition to the execution timings, in accordance with the setting order information. Finally, the medical care data indicating the respective medical care action candidates after being changed are displayed in the predetermined format, in place of or in addition to the medical care data indicating the respective medical care actions. Therefore, in such a case that there are various medical care actions which have probabilities to be executed in the future in accordance with the disease, since the disease, the pathology etc., of the pertinent patient are not known at an initial stage of the medical care schedule e.g., before the diagnosis is not confirmed, this aspect of the present invention is very convenient for making the medical care schedule.

In another aspect of the second system, the process device generates execution timing data indicating the set execution timings with respect to the object files respectively, and the object files respectively updates a stored content thereof by the generated execution timing data.

According to this aspect, the execution timing data indicating the execution timings are generated by the process device, with respect to the object files respectively. Then, the stored contents of the object files are respectively updated by the generated execution timing data. Therefore, when displaying the medical care schedule next time, it is possible to display a newest one corresponding to the stored content of the object file.

In another aspect of the second system, the display device displays the medical care data indicating the medical care action, the execution timing of which has been changed, among the plurality of medical care actions after being changed, in a display manner different from that for the medical care data indicating the medical care action, the execution timing of which has never been changed.

According to this aspect, the medical care data indicating the medical care action, the execution timing of which has been changed, are displayed by the display device, in a display manner different from that for the medical care data indicating the medical care action, the execution timing of which has never been changed. Here, the "different display manner" means to display in which a color, a brightness, a thickness or the like is different. Alternatively, a predetermined mark indicating "the change of the execution timing" may be appended to the displayed medical care data on the picture plane. For example, the changed actions are displayed in red characters while the unchanged actions are displayed in black characters. Therefore, it is possible for the medical care schedule maker to certainly recognize and confirm on the display picture plane the medical care data indicating the medical care actions, the execution timing of which has been automatically set and has been changed in accompaniment with the changing operation by the inputting device.

In another aspect of the first or second system, the input device is adapted to change the setting order information, and the process device sets the execution timing in accordance with the setting order information changed by the input device.

According to this aspect, when the setting order information included in the object file is changed by the input device, the execution timing is set by the process device in accordance with this setting order information changed by the input device. Therefore, it is possible for the medical care schedule maker to add a modification to the setting order itself by the process device in line with his or her own experience or favor. For example, it is possible to add a modification to the timing at which a specific medicine is applied after a specific medical operation.

In another aspect of the first or second system, the predetermined format is such a medical care schedule table that time units indicating at least dates are set in one of two rows and the types of the medical care actions are set in another of the two rows.

According to this aspect, the medical care data are displayed by the display device in the format of the medical care schedule table in which the time units indicating at least dates are set in one of two rows and the types of the medical care actions are set in another of the two rows. Here, the "at least dates" mean that it is allowable to include the hour, the minute, the week and so forth in addition to the date. On the other hand, the "types of the medical care actions" mean the record of the doctor or nurse, the process, the injection, the examination, the test, the evaluation, the medication, the meal (food), the practice, the monitor, the treatment, the activity restriction, the observation, the rehabilitation, the coordination, the hospitalization and the leave of hospital, the education for the family of the patient and so on. Thus, while displaying the medical care schedule table which is similar to the aforementioned conventional "care map", it is possible to automatically set the execution timings of the respective medical care actions on this medical care schedule table according to the present invention.

In another aspect of the first or second system, the predetermined format is such a list that the plurality of medical care actions, the execution timings of which are set, are arranged in an order of the execution timings regardless of the types of the medical care actions.

According to this aspect, the medical care data are displayed by the display device in the format of a list in which the plurality of medical care actions, the execution timings of which are set, are arranged in the order of the execution timings regardless of the types of the medical care actions. Therefore, while displaying the medical care schedule list, it is possible to automatically set the execution timings of respective medical care actions on the medical care schedule list.

In the aforementioned aspect of the first or second system in which the medical care data for the medical care action candidates are stored and displayed, the predetermined format may be such a decision tree that the plurality of medical care action candidates, one of which is to be disjunctively executed, are arranged in an order of the execution timing candidates.

According to this aspect, the medical care data are displayed by the display device in the format of a decision tree in which the plurality of medical care action candidates, one of which is to be disjunctively executed, are arranged in an order of the execution timing candidates. Therefore, while displaying the decision tree as indicating the existence of a plurality of candidates, it is possible to automatically set the execution timings of respective medical care action candidates on the decision tree.

In another aspect of the first or second system, the setting order information corresponding to one medical care data include before and after relation prescribing data, which respectively prescribe at least relative before and after relation of the execution timing when the medical care action indicated by the one medical care data is to be executed, with respect to an end or a start of the medical care action indicated by another medical care data as a reference.

According to this aspect, the executing timing of the medical care action indicated by one medical care data is set by the process device, in accordance with the before and after relation prescribing data, with respect to the end or the start of the medical care action indicated by another medical care data as a reference.

In another aspect of the first or second system, the setting order information corresponding to one medical care data includes time range prescribing data, which prescribe a time range during which the medical care action indicated by the one medical care data can be executed with respect to a start or an end of the medical care action indicated by another medical care data as a reference.

According to this aspect, the executing timing of the medical care action indicated by one medical care data is set by the process device, in accordance with the time range prescribing data, with respect to the end or the start of the medical care action indicated by another medical care data as a reference.

In another aspect of the first or second system, the setting order information includes execution frequency prescribing data, which prescribe an execution frequency of each medical care action.

According to this aspect, the executing timing of the medical care action indicated by the respective medical care data is set by the process device, in accordance with the execution frequency data.

In another aspect of the first or second system, each of the object files further includes intimation order information for the process device to transmit change-intimation data, which informs a change in the execution timing to another of the object files, in case that the execution timing of the medical care data included in the each of the object file is changed, and the process device transmits the change-intimation data to the another of the object files in accordance with the intimation order information and sets again the execution timings in accordance with the setting order information included in the another of the object files, in case that the execution timing is changed.

According to this aspect, when the execution timing of the medical care data included in the respective one of the object files is changed, the change-intimation data are intimated or informed by the process device to another object file in accordance with the intimation order information. By this, the execution timing is set again by the process device in accordance with the setting order information included in another object file. Therefore, in case that the execution timing of the medical care action related to one object file is changed, it is possible to automatically and speedily set again the execution timings of the medical care actions, which compose one series of medical care schedule together with this one object file.

In another aspect of the first or second system, the input device is adapted to designate at least date when at least one medical care action among the plurality of medical care actions to be executed in a future is scheduled to be executed, and the process device sets the plurality of execution timings by a unit of at least date, on the basis of the designated date.

According to this aspect, at least date when at least one medical care action is scheduled to be executed is designated by the input device. Then, on the basis of this designated date, the plurality of execution timings are set by the unit of at least date, by the process device. Namely, the respective execution timings are set by the absolute time unit such as X year, Y month, Z date, and the display on the display device is also performed by this unit of date.

In another aspect of the first or second system, the system is further provided with an alarm device for generating an alarm in case that the set plurality of executions timings are contradict to each other or in case that the execution timings which are not contradict to each other cannot be set.

According to this aspect, when the execution timings are set by the process device, in case that the set plurality of executions timings are contradict to each other or in case that the execution timings which are not contradict to each other cannot be set, the alarm is generated by the alarm device. More concretely, an alarm message may be graphically-outputted on the picture plane of the display device, or an alarm message may be audio-outputted by use of a synthetic voice. Therefore, when the medical care schedule, which is in fact impossible to perform, is almost made by the automatic setting operation according to the setting order information, the medical care schedule maker can speedily recognize the fact.

In another aspect of the first or second system, the system is provided with two units communicated to each other through a communication line, the plurality of object files are provided in one of the two units, and the display device is provided in another of the two units.

According to this aspect, the object files provided in one of the two units and the display device provided in another of the two units are connected to each other through a communication line, such as a wire line, a wireless line, an exclusive line, a general line, a telephone line and so forth. Thus, by preparing the object files in a large sized memory device provide in one unit as a center unit, and by employing such a structure that one or a plurality of other units are arranged as terminal apparatuses, it becomes possible to commonly use or share the same data between the plurality of terminal apparatuses. In addition, the input device may be provided in another of the two units (i.e., the terminal apparatus) in the same manner as the display device. The process unit may be provided in one or another of the two units.

In another aspect of the first or second system, the predetermined format is such a medical care schedule table that time units indicating at least dates are set in one of two rows and the types of the medical care actions are set in another of the two rows, each of the object files includes multiple correlation information, which indicates multiple correlations between each of the object files and the respective type or types in another of the two rows and indicates a priority order of the multiple correlations, and the process device correlates the object files with respective one of the types set in another of the two rows in the displayed medical care schedule table, in accordance with the multiple correlation information.

According to this aspect, when the medical care data are displayed in the format of the medical care schedule table, the object files are correlated with respective one of the types in the displayed medical care schedule table, in accordance with the multiple correlation information which is included in each of the object files. Thus, each of the object files is correlated to an appropriate row in the table so that the medical care data included in each of the object file can be displayed in an appropriate row of the table. Even if the most appropriate type of the medical care action is not present in the table, the object file can be still correlated to a satisfactory row according to the priority number in the multiple correlation information, so that the medical care data can be displayed in the medical care schedule table.

In another aspect of the first or second system, the predetermined format is such a medical care schedule table that time units indicating at least dates are set in one of two rows and the types of the medical care actions are set in another of the two rows, and the process device thins out the type or types in another of the two rows, to which no object file is corresponding to, in the displayed medical care schedule table.

According to this aspect, when the medical care data are displayed in the format of the medical care schedule table, the type or types in another of the two rows, to which no object file is corresponding to, are thinned-out (omitted) in the displayed medical care schedule table. Thus, since there exists no empty row (e.g., no empty horizontal row or line), which is less important in the table, it is relatively easy to see the important or meaningful portion of the table within the picture plane having a limited size of the display device.

In another aspect of the first or second system, the predetermined format is such a medical care schedule table that time units indicating at least dates are set in one of two rows and the types of the medical care actions are set in another of the two rows, and the process device thins out the date or dates in one of the two rows, to which no object file is corresponding to, in the displayed medical care schedule table.

According to this aspect, when the medical care data are displayed in the format of the medical care schedule table, the time units in one of the two rows, to which no object file is corresponding to, are thinned-out (omitted) in the displayed medical care schedule table. Thus, since there exists no empty row (e.g., no empty vertical row or column), which is less important in the table, it is relatively easy to see the important or meaningful portion of the table within the picture plane having a limited size of the display device.

The above object of the present invention can be also achieved by a first program storage device readable by a system for aiding to make a medical care schedule, tangibly embodying a program of instructions executable by the system to perform method processes for aiding to make a medical care schedule, the system comprising: a plurality of object files respectively including (i) medical care data indicating either one of a plurality of types of medical care actions which are set in advance and (ii) setting order information to set at least relative execution timings as for the plurality of medical care actions, which compose one series of medical care schedule. The method processes are provided with the processes of: setting, when the plurality of medical care actions composing one series of medical care schedule are designated, the at least relative execution timings of the designated plurality of medical care actions on a predetermined time axis, in accordance with the setting order information respectively included in the plurality of object files, which include the plurality of medical care data indicating the designated plurality of medical care actions; and displaying a plurality of medical care data respectively indicating the plurality of medical care actions, the at least execution timings of which are set by the setting process, in such a predetermined format that the medical care actions are respectively arranged in an order of the execution timings.

According to the first program storage device, such as a CD-ROM, a ROM, a DVD, a floppy disk or the like, of the present invention, the above described first system of the present invention can be realized as it reads and executes the program of instructions.

The above object of the present invention can be also achieved by a second program storage device readable by a system for aiding to make a medical care schedule, tangibly embodying a program of instructions executable by the system to perform method processes for aiding to make a medical care schedule, the system comprising: a plurality of object files respectively including (i) medical care data indicating either one of a plurality of types of medical care actions which are set in advance, (ii) setting order information to set at least relative execution timings as for the plurality of medical care actions, which compose one series of medical care schedule and (iii) execution timing data indicating at least relative execution timings of respective one of the medical care actions indicated by the medical care data on a predetermined time axis. The method processes are provided with the processes of: displaying a plurality of medical care data respectively indicating the plurality of medical care actions, the at least execution timings of which are set, in such a predetermined format that the medical care actions are respectively arranged in an order of the execution timings, on the basis of the execution timings indicated by the stored execution timing data; changing at least partially the medical care actions and/or the execution timings in a condition where the medical care data are displayed in the predetermined format; setting the execution timings of the respective medical care actions after being changed in accordance with the setting order information included in the object files, which include the medical care data indicating the respective medical care actions after being changed, and displaying the medical care data indicating the respective medical care actions after being changed in the predetermined format, on the basis of the execution timings set by the setting process.

According to the second program storage device, such as a CD-ROM, a ROM, a DVD, a floppy disk or the like, of the present invention, the above described second system of the present invention can be realized as it reads and executes the program of instructions.

The nature, utility, and further features of this invention will be more clearly apparent from the following detailed description with respect to preferred embodiments of the invention when read in conjunction with the accompanying drawings briefly described below.

BRIEF DESCRIPTION OF THE DRAWINGS

FIG. 2 is a plan view showing one example of a table which is graphically outputted by the first embodiment;

FIG. 3 is a plan view showing one example of a list which is graphically outputted by the first embodiment;

FIG. 10 is a conceptional diagram of an operation to change the schedule in a condition where the table of FIG. 2 is displayed, by using a plurality of object files in the first embodiment;

FIG. 11 is a plan view showing another example of a table which is graphically outputted by the first embodiment;

FIG. 18 is a conceptional diagram of an operation to change the schedule in a condition where the decision tree of FIG. 15 is displayed, by using a plurality of object files in the second embodiment;

FIG. 20 is a conceptional diagram showing an operation principle of a system for aiding to make a medical care schedule as a fourth embodiment of the present invention;

FIG. 21 is another conceptional diagram showing an operation principle in the fourth embodiment; and FIG. 22 is a diagram showing functions of the medical care navigation system of the embodiments.

DETAILED DESCRIPTION OF THE PREFERRED EMBODIMENTS

Referring to the accompanying drawings, embodiments of the present invention will be now explained.

(I) First Embodiment

Figure 1:
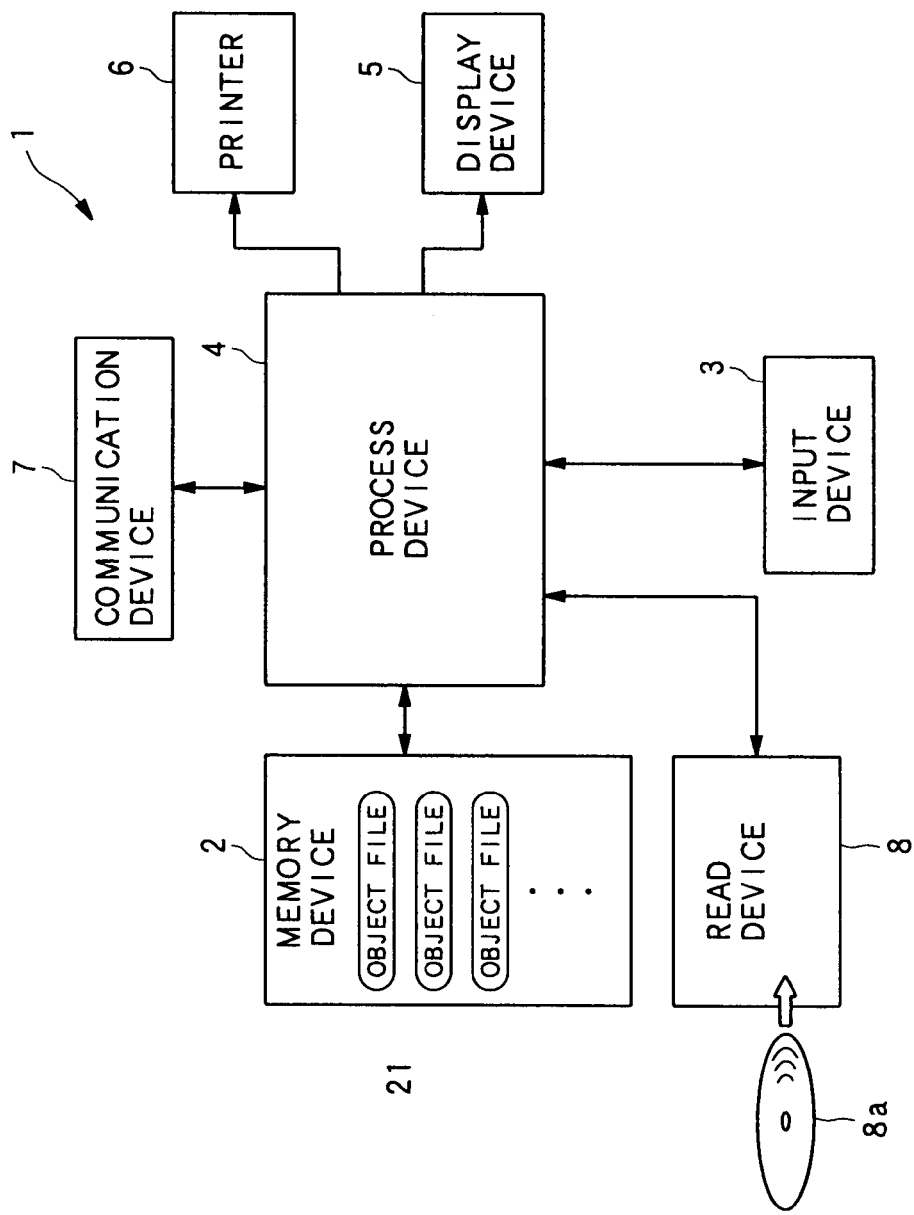
FIG. 1 is a block diagram of a system for aiding to make a medical care schedule as a first embodiment of the present invention.

FIG. 1 shows a block diagram of a system for aiding to make a medical care schedule as a first embodiment of the present invention.

In FIG. 1, a system 1 for aiding to make a medical care schedule may consist of, as a hardware resource, a personal computer, a work station, a middle size computer, a large size computer, a mobile computer (i.e., a hand-carry type information terminal), an electronic diary or the like, and is provided with: a memory device 2; an input device 3; a process device 4; a display device 5; a printer 6; a communication device 7; and a read device 8.

The memory device 2 is preferably a known large data volume memory device of randomly accessible type, such as a hard disc device, an IC (Integrated Circuit) memory, a magnetic disc device, an optical disc device or the like.

In the memory device 2, there are constructed a plurality of object files 21, each including: medical care data indicating either one of a plurality of kinds of medical care actions which are set in advance; and setting order information for setting at least relative execution timing (the phase or the when) to execute respective one of the plurality of medical care actions composing one series of medical care schedule.

The input device 3 is provided with a key board, a ten key switch, a mouse, a track ball, an input pen, an input tablet or the like, and is adapted to specify or designate an arbitrary position on the image displayed on the display device 5. The input device 3 is especially adapted to specify or designate the plurality of medical care actions composing one series of medical care schedule and to input various kinds of data and command other than that.

The process device 4 has a CPU (Central Processing Unit), and is constructed to set, when the plurality of medical care actions composing one series of medical care schedule are designated, the at least relative execution timings of the designated plurality of medical care actions on a predetermined time axis in accordance with the setting order information included in the plurality of object files 21, which include the plurality of medical care data respectively indicating the designated plurality of medical care actions.

The display device 5 may be a known display device such as a CRT (Cathode Ray Tube) display device, an LCD (Liquid Crystal Display) device or the like, and is especially constructed such that an arbitrary position on its picture plane can be designated by the input device 3. The display device 5 displays at least the plurality of medical care data indicating the plurality of medical care actions whose execution timings are designated, by a predetermined format in which the respective medical care actions are arranged in the order of execution timings.

The predetermined format for displaying the medical care data in this manner is, for example, a format of a medial care schedule table, in which medical care actions of various types are arranged in first rows for each type of the medical care actions and in second rows orthogonal to the first rows for each time unit indicating at least date (e.g., the aforementioned care map as described in U.S. patent application Ser. No. 08/746,175 now U.S. Pat. No. 5,913,197. Here, "at least date" means that hour, minute, week and so forth may be included in addition to the date. On the other hand, the "types of the medical care actions" may be the record by the doctor or nurse, the process, the injection, the examination, the test, the evaluation, the medication, the meal (food), the practice, the monitor, the treatment, the activity restriction, the observation, the rehabilitation, the coordination, the hospitalization and the leave of hospital, the education for the family of the patient and so on. One example of a display by such a format of the medical care schedule table is shown in FIG. 2.

In FIG. 2, the medical care data are displayed on the display device 5 by the format of a medical care schedule table 10 in which date is set on an abscissa 12 while the type of the medical care action is set on an ordinate 11 (i.e., a vertical axis). In this case, while displaying the medical care schedule table 10 in the same manner as the aforementioned "care map", it is possible to execute an automatic setting process of execution timings of the medical care actions on the medical care schedule table 10, by using the object files 21.

As shown in FIG. 3, the predetermined format for displaying the medical care data may be a format of a list 110 in which the plurality of medical care actions, whose execution timings are set, are arranged in the order of the execution timings regardless of the type of the medical care actions (in the example shown in FIG. 3, in the order of date and in the order of time as for the medical care actions included in each category of the medical care actions on the same date). In this case, while displaying the medical care schedule list 110, it is possible to execute an automatic setting process of execution timings of the medical care actions on the medical care schedule list 110, by using the object files 21. In case of this format, a portion 112 corresponding to the unit of date in the medical care schedule list 110 may be displayed while feeding a page for each picture plane, or may be scrolled up and down direction while indicating a division line of the portion 112 by a dotted line or the like.

Incidentally, format information and a program for displaying, which are necessary to display the medical care data in the above mentioned format shown in FIG. 2 or FIG. 3, by the process device 4 and the display device 5, may be included in a computer program which is stored in a record medium 8a in advance.

In FIG. 1 again, the printer 6 may be a known printer such as a laser beam printer, an ink jet printer or the like, and may be a color type or a black and white type. The printer 6 prints the medical care data by the format shown in FIG. 2 or FIG. 3, for example.

The communication device 7 is provided with a modem etc., to perform a data communication of various files including the object files 21 and data with another computer or the like. The communication device 7 is connected with other large size computer, personal computer, mobile computer (i.e., a hand-carry type information terminal), an electronic diary and the like, through a communication line, such as a wire-line, a wireless-line, an exclusive line, a general line, a telephone line and so on.

The reading device 8 may include a CD-ROM drive, a DVD-ROM drive and an FD (Floppy or Flexible Disk) drive for reading a computer program recorded on a record medium 9, such as a CD-ROM, a DVD-ROM and an FD respectively, for example. The computer program read in this manner allows the computer i.e., the hardware resource of the system 1 to function as the system for aiding to make the medical care schedule. One or whole portion of the object files 21 constituted in the memory device 2 may be recorded on the record medium 8a, and may be read out as the occasion demand. Especially, it is convenient later to store in advance (i) the object files 21, which are used for a standard medical care schedule at a stage before making an individual medical care schedule for a specific patient, or (ii) the standard object files 21, from which as the base the individual medical care schedule can be modified or changed, to the record medium 8a together with the computer program since they can be produced at the time of producing the computer program and since their flexibility is high.

Next, the concrete logical structure of the object files 21, which are logically constituted in the memory device 2, is explained with reference to FIG. 4.

Figure 4:
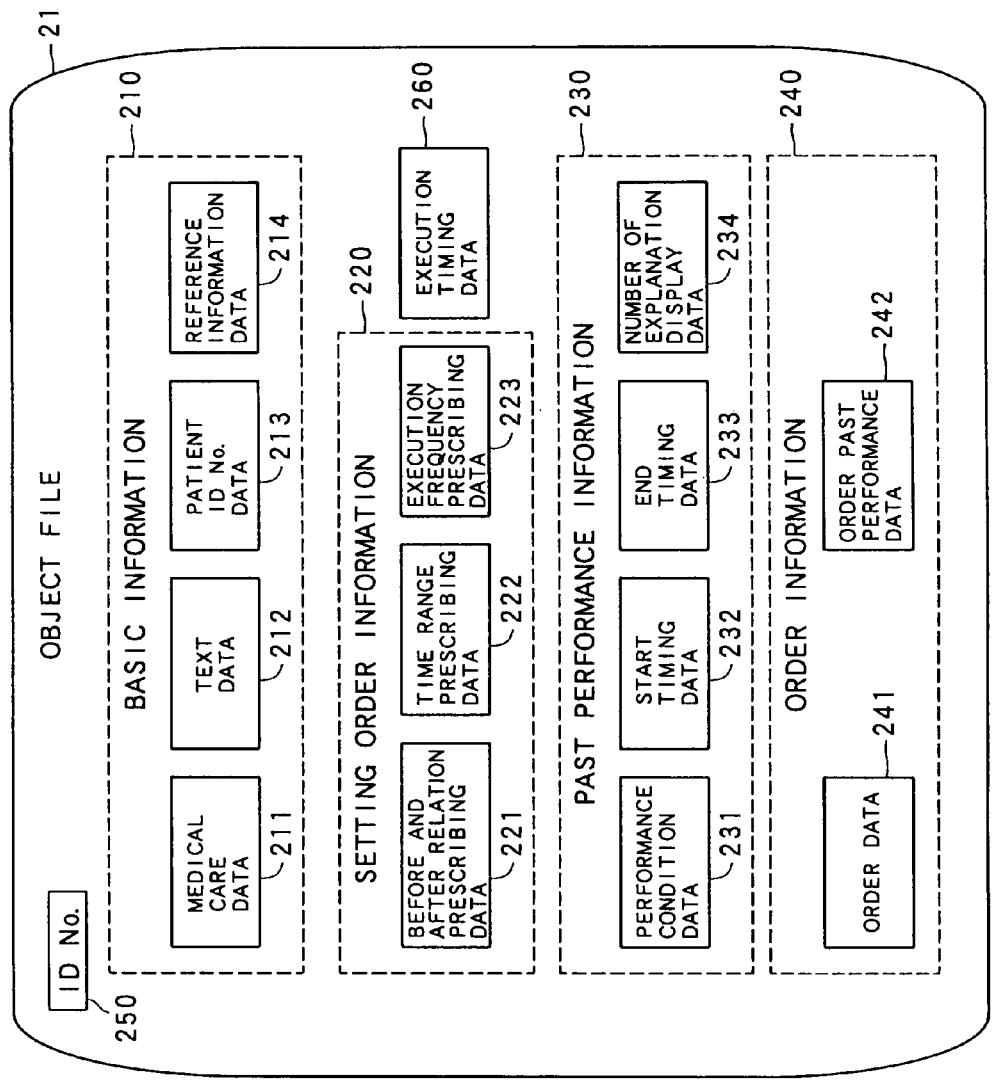
FIG. 4 is a schematic diagram showing a structure of an object file constituted in the memory device of the first embodiment.

As shown in FIG. 4, the object file 21 includes basic information 210, which includes aforementioned medical care data 211, and setting order information 220.

At first, the basic information 210 is explained.

In FIG. 4, the basic information 210 includes the medical care data 211 indicating one of the plurality of types of medical care actions set in advance. Here, "the types of medical care actions" means the record by the doctor or nurse, the process, the injection, the examination, the test, the evaluation, the medication, the meal (food), the practice, the monitor, the treatment, the activity restriction, the observation, the rehabilitation, the coordination, the hospitalization and the leave of hospital, the education for the family of the patient and so on, as for large categories, and further means more concrete individual actions in each of the large categories respectively (e.g., indicating what kind of injection, examination, medication, operation etc., is to be executed). Therefore, the medical care data 211 in each of the object files 21 indicate the category and the concrete action in the respective category by use of category codes in predetermined digits for example. As such category codes, category codes which are world-widely or domestically used (e.g., the ICD code, the clinical payment point code) may be adapted, or a category code exclusive for the present invention may be adapted. In summary, as long as the medical care actions are categorized by use of categories suitable for the medical care schedule in the actual and current medical care field, the technical subject of the present invention can be achieved, so that the categorizing method itself is flexible in the present embodiment.

The basic information 210 includes, in addition to the medical care data 211, text data 212, which show a short word or sentence for explaining the detail of the medical care action indicated by the corresponding medical care data 211 to a person who is making the medical care schedule, and also shows a short word or sentence for explaining the medical care action indicated by the corresponding medical care data 211 to the patient. Further, the basic information 210 includes, in case that the pertinent object file 21 is used as one portion of the medical care schedule for a specific patient or a virtual patient having a specific disease, (i) a patient ID (Identification) number data 213 indicative of the ID number of the specific or virtual patient and (ii) reference information data 214 related to the medical care data as for the pertinent object file 21. The reference information data 214 are detailed medical care data accompanying with the medical care action indicated by the medical care data 211 corresponding to each of the object files 21. For example, the reference information data 214 may be numerical data related to a predetermined type of medical care action such as body temperature data, blood pressure data, concentration data of predetermined component in blood and the like, which are daily measured.

Next, the setting order information 220 is explained. The setting order information 220 is information to respectively set the at least relative execution timings as for the plurality of medical care actions composing one series of medical care schedule. Here, the "relative execution timing" means a timing when one medical care action is to be executed with respect to the execution timing of another medical care action. For example, it indicates that one medical care action is to be executed before or after another medical care action, how many days or hours before, or how many days or hours after another medical care action, or the frequency of the pertinent medical care action.

In FIG. 4, the setting order information 220 includes before and after relation prescribing data 221, which prescribe an at least relative before and after relationship of the execution timing of the medical care action indicated by the medical care data 210 included in the object file 21 with respect to the end or start of the medical care action indicated by the medical care data 210 included in another object file 21 as a standard. Thus, in the present embodiment, the execution timing of the medical care action indicated by respective one of the medical care data 211 is set by the process device 4 as the occasion demands in accordance with this before and after relation prescribing data 221.

The setting order information 220 includes, in addition to the before and after relation prescribing data 221, time range prescribing data 222, which respectively prescribe a time range in which the medical care action indicated by the medical care data 211 included in the pertinent object file 21 can be executed with respect to the end or start of the medical care action indicated by the medical care data 211 included in another object file 21. Thus, in the present embodiment, the execution timing of the medical care action indicated by respective one of the medical care data 211 is set by the process device 4 as the occasion demands in accordance with this time range prescribing data 222. Further, the setting order information 220 includes, in addition to these before and after relation prescribing data 221 and the time range prescribing data 222, execution frequency prescribing data 223, which respectively prescribe an execution performance frequency of each of the medical care data 211. Thus, in the present embodiment, the execution timing of the medical care action indicated by respective one of the medical care data 211 (e.g., how many times it is executed per day) is set by the process device 4 as the occasion demands in accordance with this execution frequency prescribing data 240.

In FIG. 4, especially in the present embodiment, the object file 21 further includes past performance information 230. This past performance information 230 is to make the object file 21, which indicates one medical care action in the medical care schedule, function as a performance record file including the medical care data 211 on the past record base after the medical care action has been actually performed. More concretely, the past performance information 230 includes: past performance condition data 231 of 1 bit indicating whether the medical case action corresponding to the pertinent object file 21 is on the forecast (schedule) base or on the past performance record base; start timing data 232 and end timing data 233 respectively indicating the start timing and the end timing in case that the corresponding medical care action has been actually performed; and number of explanation display data 234 indicating the number of times of the explanation to the patient by use of explanation data for the patient included in the pertinent object file 21.

In FIG. 4, especially in the present embodiment, the object file 21 includes order information 240. The order information 240 includes order data 241 to make it possible to link the pertinent system for aiding to make the medical care schedule with a known ordering system as explained later. If the order data 241 are described in each of the object file 21, the order such as an examination reservation, a hospitalization reservation, an operation reservation etc., can be performed in linkage with the medical care action indicated by the medical care data 211 included in each of the object files 21. Further, the order information 240 includes order past performance data 242 indicating a fact that the corresponding order has been actually performed.

To each of the object files 21, ID number data 250 having a predetermined digit peculiar to respective one of the object file is given, so that it is possible for the process device 4 in FIG. 1 to search an arbitrary object file 21 by use of the ID number data 250. Further, in case that a new object file 21 is made, new ID number data 250 is given to this new object file 21.

Each of the object files 21 further includes execution timing data 260. When each execution timing is set by the process device 4 in accordance with the setting order information 220 as a result of designating the medical care actions composing one series of medical care schedule or modifying the medical care schedule, the execution timing data 260 are generated by the process device 4 as data indicating this set execution timing, and are stored in the pertinent object file 21. Therefore, in case that the pertinent object file 21 does not relate to the setting of the execution timing, this execution timing data may not exist or a predetermined default value may be stored as it. Contrary to this, in case that the execution timing are once set or set again, when the medical care data are to be displayed by using the pertinent object file 21, it is enough to follow the execution timing data 260 as for the execution timing, so that it is not necessary to repeat the same setting operation.

Figure 5:
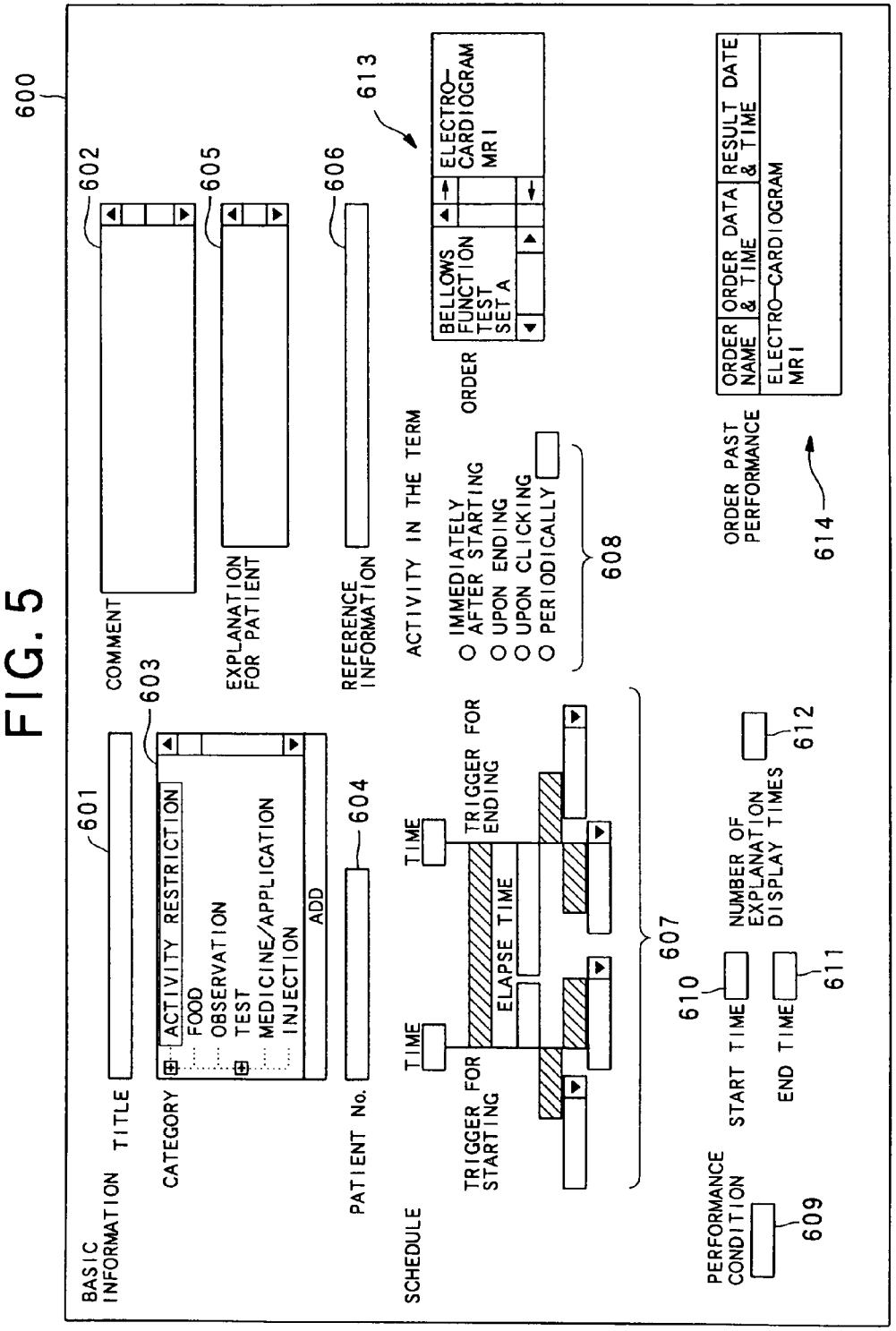
FIG. 5 is a plan view showing an input picture plane when referring to, newly inputting, changing the object file or the like in the first embodiment.

Next, the referring, newly composing and content-changing operations of the object file 21 including the above described various data are explained with reference to FIG. 4 and FIG. 5. FIG. 5 shows an input picture plane 600, which is displayed on the display device 5 at the time of the referring, newly composing and content-changing operations. Text data, numerical data, codes etc., displayed in each field of the input picture plane 600 are composed as a predetermined command is executed by designating a specific medical care action in the medical care schedule table 10 shown in FIG. 2 with a cursor, on the basis of the basic information 210, the setting order information 220, the past performance information 230 and the order information 240 included in the object file 21 corresponding to this medical care action (refer to FIG. 4).

Especially, the present embodiment is constructed such that the change including newly-inputting and erasing of the data displayed in each field on the input picture plane 600 shown in FIG. 5 can be performed through the input device 3 (refer to FIG. 1).

The medical care action indicated by each of the medical care data 211 which compose one portion of the basic information 210 and are categorized in predetermined codes (refer to FIG. 4) is displayed in a "title" field 601 as text data showing a short word or sentence as the master file stored in advance in the memory device 2 for the code conversion is referred to, for example in FIG. 5. In a "comment" field 602 which is located on a right side thereof, in case that each of the medical care actions cannot be determined only according to the title, the text data showing a short word or sentence for commenting or explaining the content of the medical care action in detail are displayed on the basis of the text data 212 which composes one portion of the basic information 210 (refer to FIG. 4). In a "category" field 603, the categories of the medical care actions are listed up, among which the category corresponding to the medical care action displayed in the "title" field is highlight-displayed. Especially, in the "category" field 603, by the cursor movement by use of the input device 3 etc., various medical care actions which are prepared in a hierarchy manner can be designated, so that it is possible to speedily define an arbitrary medical care action with respect to each f the object files 21. In a "patient number" field 604, in case that the pertinent object file 21 is used when the medical care schedule is to be actually made with respect to a specific patient or a virtual patient having a specific disease, the patient ID number of that specific or virtual patient is displayed on the basis of the patient ID number data 213 composing one portion of the basic information 210 (refer to FIG. 4). Further, in an "comment for the patient" field 605, the text data showing a short word or sentence for commenting or explaining the content of the medical care in an easily understandable manner for the patient are displayed on the basis of the text data 212 composing one portion of the basic information 210 (refer to FIG. 4). In a "reference information" field 606, the existence of the detail information, which can be referred to when each of the object file 21 is actually used as one portion of the medical care schedule, is displayed by its title, its ID number or the like, on the basis of the reference information data 214 composing one portion of the basic information 210 (refer to FIG. 4).

Therefore, the medical care schedule maker such as a medical doctor can easily refer to, newly input and change the medical care data, the patient ID number data and so forth by use of each of the fields 601 to 606 based on the various data included in the basic information 210 (refer to FIG. 4), and can easily refer to, newly input and change the text data corresponding to the medical care data.

In FIG. 5, in a "schedule" field 607, a start time of the medical care action indicated by the medical care data 211 included in the pertinent object file 21, a trigger for starting it (e.g., another medical care action related thereto, a start instruction), an end timing, a trigger for ending it (e.g., another medical care action related thereto, an end instruction) and the elapse time are displayed, on the basis of the before and after relation prescribing data 221, the time range prescribing data 222 and the executing frequency prescribing data 223 which compose the setting order information 220 (refer to FIG. 4) as well as the execution timing data 260. In an "activity in the term" field 608, whether the setting process of the execution timing by the process device 4 on the basis of the setting order information 220 included in the pertinent object file 21 is performed immediately after the start of the medical care action, at an end timing, at time of clicking a predetermined item on the display picture plane of the medical care schedule in the predetermined format described later or periodically executed is displayed by a black circle, on the basis of the before and after relation prescribing data 221, the time range prescribing data 222 and the execution frequency prescribing data 223 (refer to FIG. 4).

Therefore, the medical care schedule maker such as a medical doctor can easily refer to, newly input and change the before and after relation prescribing data 221, the time range prescribing data 222 and the execution frequency prescribing data 223 by use of each of the field 607 and 608 based on the various data included in the setting order information 220 (refer to FIG. 4). Then, after the setting order information 220 included in each of the object file 21 is changed, the execution timing is set by the process device 4 in accordance with the setting order information 220 after the change. Thus, the medical care schedule maker can apply the modification onto the setting order by the process device 4 itself in line with his or her experience and/or favorite. For example, it is possible to apply a modification onto the timing of medicating a specific medicine after a specific medical operation. Incidentally, when the execution timing is set once or set again, the newest execution timing data 260 indicating the set or reset execution timing is stored in the object file 21. Further, in accordance with the newest execution timing data 260, the start time, the end timing and the like are updated on the input picture plane 600.

In FIG. 5, in a "past performance condition" field 609, whether the medical care action corresponding to the pertinent object file 21 has been already executed or not is shown on the basis of the past performance condition data 231 composing one portion of the past performance information 230 (refer to FIG. 4). In case that the medical care action has been already executed, the start time (which may also include the date) is displayed in the "start time" field 610 on the basis of the start timing data 232 while the end timing (which may also include the date) is displayed in the "end time" field 611 on the basis of the end timing data 233.

Accordingly, the medical care schedule maker such as a medical doctor can easily input the past performance information by using each of the fields 609 to 611 and can easily search the information later, when the medical care action indicated by the medical care data included in the pertinent object file 21 is executed in an medical care schedule by using the object files 21.

In an "number of explanation display times" field 612, the number of times that the explanation has been performed with respect to the patient is shown by use of the comment data for the patient included in the object file 21, on the basis of the number of explanation display data 234 included in the pertinent object file 21 (refer to FIG. 4).

Accordingly, the medical care schedule maker such as a medical doctor can speedily recognize whether he or she has certainly explained or explained enough to the patient with respect to the same medical care action, just by referring to the "number of explanation display times" field 612 later, after inputting the number of times each time when the explanation is actually made to the patient. In this manner, the present embodiment is convenient from the view point of the informed concept, and is also convenient as a proof showing the fact for the discussion whether it has been really explained or not.

In an "order" field 613, a black circle mark is displayed depending upon whether or not the corresponding order is to be performed on the basis of the order data 241 composing one portion of the order information 240, and an item to be ordered is displayed in case that the order is to be performed. Further, in an "order past performance" field 614, the name of the order which has been actually performed, the date and/or time when each order has been requested, the date and/or time when the order has been performed and the like, are displayed on the basis of the order past performance data 242.

Therefore, the medical care schedule maker such as a medical doctor can make a good use of the "order" field 613, so as to allow the aiding system 1 of the present embodiment to function as an conventional ordering system, which speeds up starting an operation such as a medicine preparation, an accounting, etc., by promptly sending the information to a terminal device at each division in the hospital. Further, by referring to the "order past performance" field 614, it is possible to easily recognize whether or not each order has been certainly performed.

In the above explanation with reference to FIG. 5, although the basic information 210, the setting order information 220 etc., included in the object file 21 are newly inputted and changed on the input picture plane 600, at least one portion of these information may be newly inputted and/or changed on the picture plane showing the medical care schedule in the format shown in FIG. 2 or FIG. 3 other than the input picture plane 600. Further, at least one portion of the information may be newly inputted and/or changed by window-displaying a menu picture plane or the like for inputting and changing the information in the picture plane of the medical care schedule in the format shown in FIG. 2 or FIG. 3. Even in case that the basic information 210, the setting order information 220 etc., are newly inputted or changed on the picture plane other than the input picture plane 600, the storage content of the object file 21 is updated. If the input picture plane 600 is displayed after that, the newest various data corresponding to the storage content of the update object file 21 are displayed.

Next, the automatic setting operation of the execution timings and the displaying operation based on the setting result in the system for aiding to make the medical care schedule constructed in the above described manner are explained.

Figure 6:
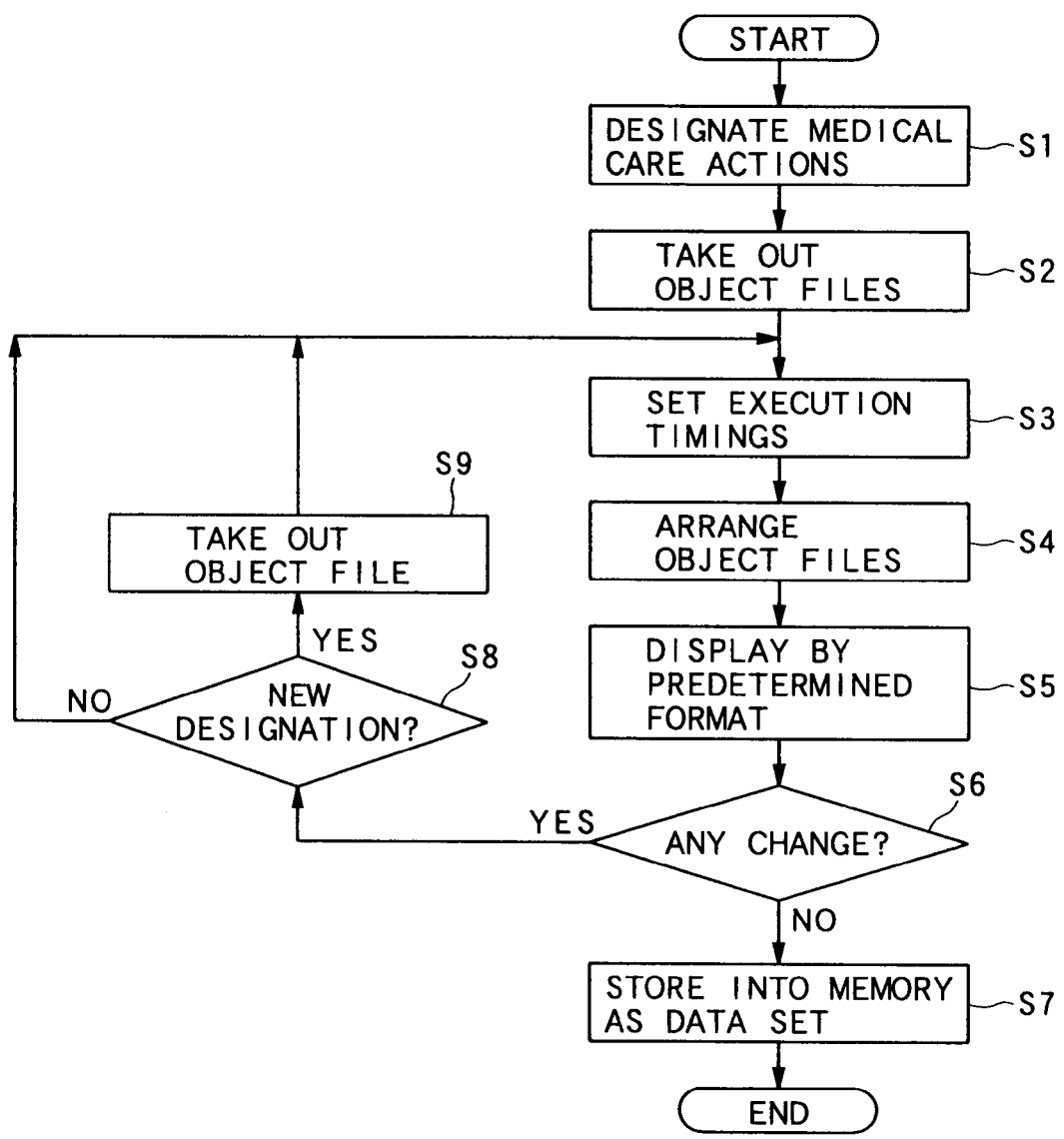
FIG. 6 is a flow chart showing an operation to construct and display the table of FIG. 2 or the list of FIG. 3 by using a plurality of object files in the first embodiment.
Figure 7:
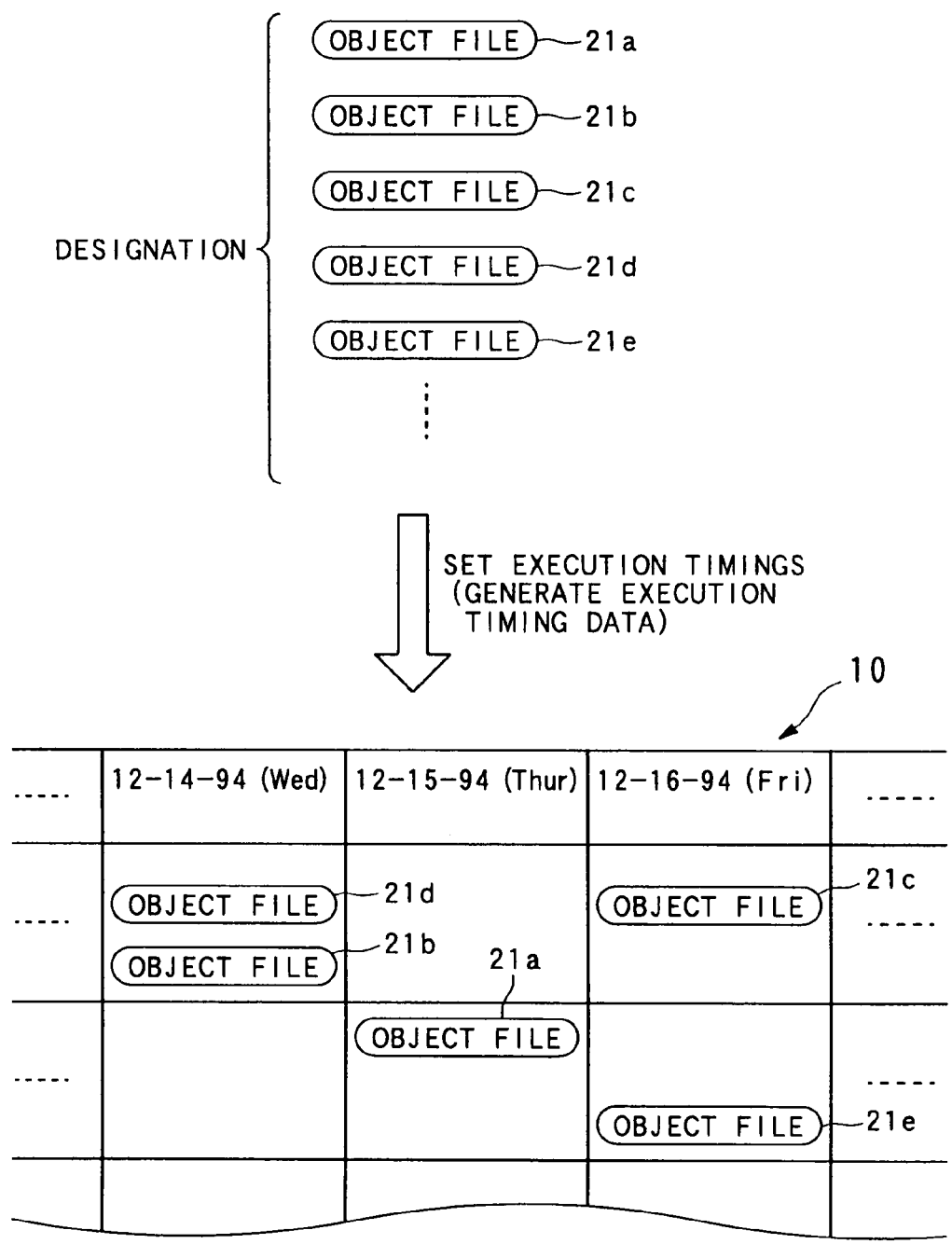
FIG. 7 is a conceptional diagram of an operation to construct and display the table of FIG. 2 by using a plurality of object files in the first embodiment.
Figure 8:
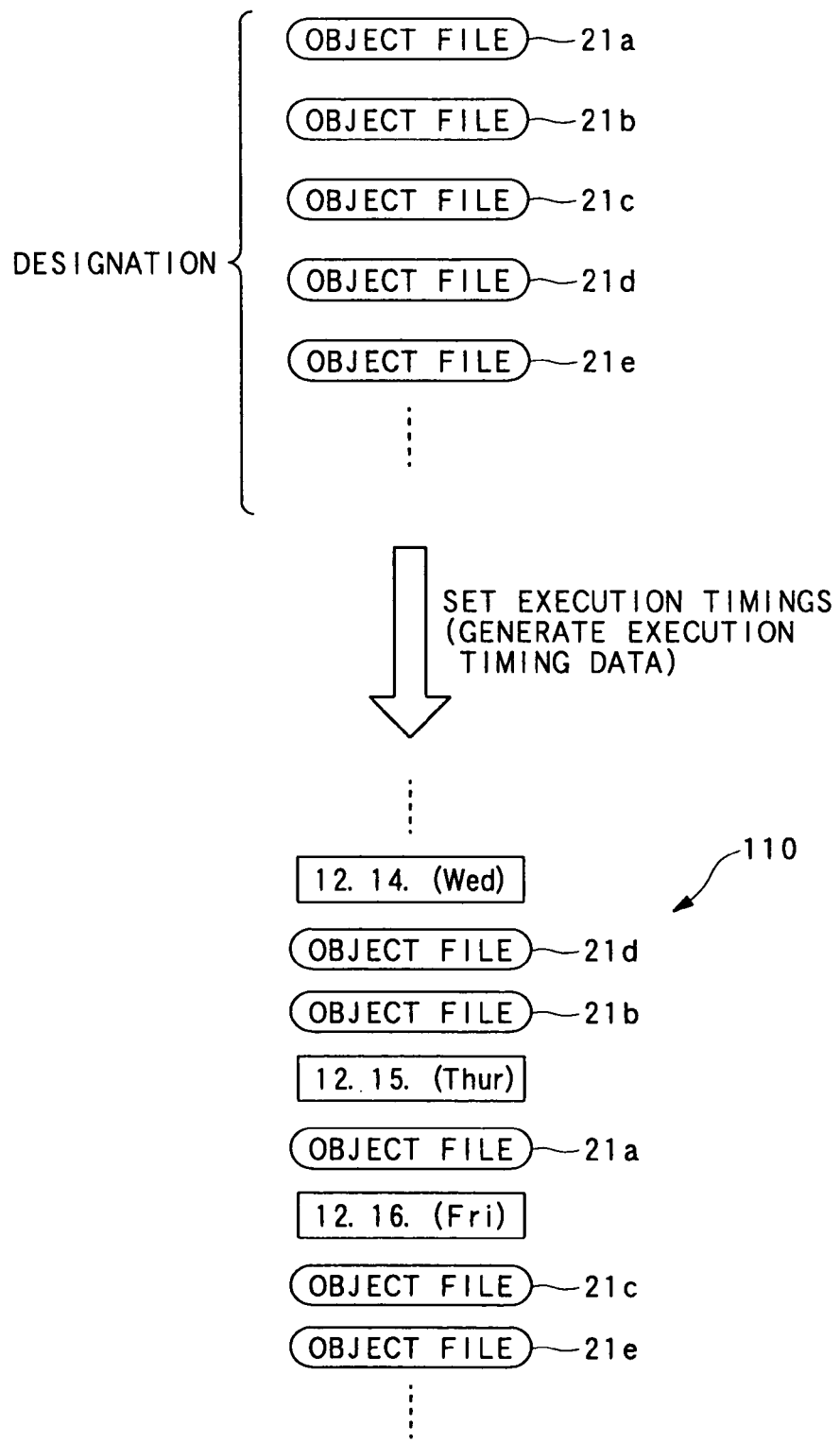
FIG. 8 is a conceptional diagram of an operation to construct and display the list of FIG. 3 by using a plurality of object files in the first embodiment.

At first, the operation of newly making the medical care schedule composed of various data included in the plurality of object files 21 are explained with reference to FIG. 6 to FIG. 8. Here, FIG. 6 is a flow chart showing this operation. FIG. 7 is a conceptional diagram in case that the medical care schedule table 10 in FIG. 2 is made and displayed by use of the plurality of object files 21. FIG. 8 is a conceptional diagram in case that the medical care schedule list 110 in FIG. 3 is made and displayed by use of the plurality of object files 21.

In FIG. 6, when making the medical care schedule, at first, a plurality of medical care actions composing one series of medical care schedule are designated one by one by an inputting operation through the input device 3 such as a keyboard, a mouse and the like (refer to FIG. 1), or are designated at once by an inputting operation through the memory device 2 or the reading device 1 such as a hard disc, a floppy disk and the like (refer to FIG. 1) (step S1). Then, a plurality of object files 21a, 21b, 21c, 21d, 21e, . . . corresponding to the designated medical care actions are taken out from the memory device 2, by the process device 4 (refer to FIG. 1) (step S2, refer to upper portions of FIG. 7 and FIG. 8).

Then, at least the relative execution timings of the designated medical care actions on the predetermined time axis are set in accordance with the setting order information 220 respectively included in the object file 21 (refer to FIG. 4), by the process device 4 (step S3). Here, to set at least the relative execution timings means both of to set the concrete date, i.e., which year, which month and which date, and to set how many days before or after with respect to the hospitalization date, the medical operation date etc., for example as a standard date.

Then, when the execution timings are set in this manner, the object files 21 are respectively made into the object files 21a, 21b, 21c, 21d, 21e, . . . which are arranged in correspondence with the data filing each cell of the medical care schedule table 10 shown in FIG. 2, according to the types of the medical care actions and the set execution timings for example (step S4, refer to a lower portion of FIG. 7). Alternatively, when the execution timings are set in this manner, the object files 21 are respectively made into the object files 21a, 21b, 21c, 21d, 21e, . . . which are arranged in correspondence with the data filling each line of the medical care schedule list 110 shown in FIG. 3, according to the types of the medical care actions and the set execution timings for example (step S4, refer to a lower portion of FIG. 8).

In this way, as the medical care schedule maker such as a medical doctor performs an operation to designate a plurality of medical care actions composing one series of the medical care schedule without designating the execution timings, the at least relative execution timings are automatically set according to the setting order information 220 included in each of the object files 21 (refer to FIG. 4), and the medical care data 211 are displayed in the format shown in FIG. 2 or FIG. 3 on the basis of the automatically set execution timings (step S5). Thus, even in case that a plurality or large number of medical care actions which are complicatedly related with each other compose one series of medical care action, it is possible to easily and speedily make the medical care schedule in which the before and after relation between the plurality of medical care actions and the timing relationship are appropriately prescribed.

At this occasion, since the knowledge as for the execution timings is not required for the medical care schedule maker, the medical care schedule maker who is not veteran or well experienced can still easily and speedily make the appropriate medical care schedule, which is very convenient. Further, in case that a plurality of medical care actions are newly designated by adding, changing or erasing the medical care actions for example, with respect to a plurality of medical care actions composing one series of medical care schedule which have been once made, since the execution timings of medical care actions can be set according to the setting order information 220 included in the object files 21, it is not necessary for the medical care schedule maker such as a medical doctor to perform troublesome operations which require labors and certain time such as operations to shift the execution timings of medical care actions one by one, which is very advantageous.

Next, it is monitored by the process device 4 whether or not the input operation, which indicates the change of the displayed medical care action and/or execution timing, is performed through the input device 3 (step S6). If there is no input operation indicating the change (step S6: NO), the medical care schedule which is currently displayed is confirmed by the medical care schedule maker, so that the plurality of object files 21 corresponding to the display content at this stage are stored as one data set into the memory device 2, while being correlated with the patient code, the disease code and/or the patient attribute code (step S7). Then, the process is ended. On the other hand, if there is the input operation indicating the change (step S6: YES), it is judged by the process device 4 whether or not a medical care action which has never been displayed is newly designated (step S8). Then, in case that there is no new designation, i.e., in case that only the execution timing of the medical care action is changed (step S8: NO), the operation flow returns to the step S3, and the re-setting of the execution timing is performed by using the setting order information 220 (step S3). On the other hand, in case there is the new designation (step S8: YES), the object file 21 corresponding to this medical care action which is newly designated is taken out from the memory device 2 (step S9), and the operation flow returns to the step S3. Then, the re-setting of the execution timings by use of the setting order information 220 is performed (step S3).

As described above, when making the medical care schedule, the medical care actions for a virtual patient, who has a specific disease such as a stomach cancer, angnapctori or the like for example, as the medical care actions composing one series of the medical care schedule are designated. Namely, in this case, it is possible to make a standard or institutional medical care schedule in advance which is supposed to be the optimum for each disease. Alternatively, the medical care actions for a specific patient who has been actually examined for hematemesis, deterioration of visual acuity, a high body temperature etc., as the medical care actions composing one series of medical care schedule are designated. Namely, in this case, it is possible to make a standard or institutional medical care schedule in a real time manner which is supposed to be the optimum for the individual patient.

Figure 9:
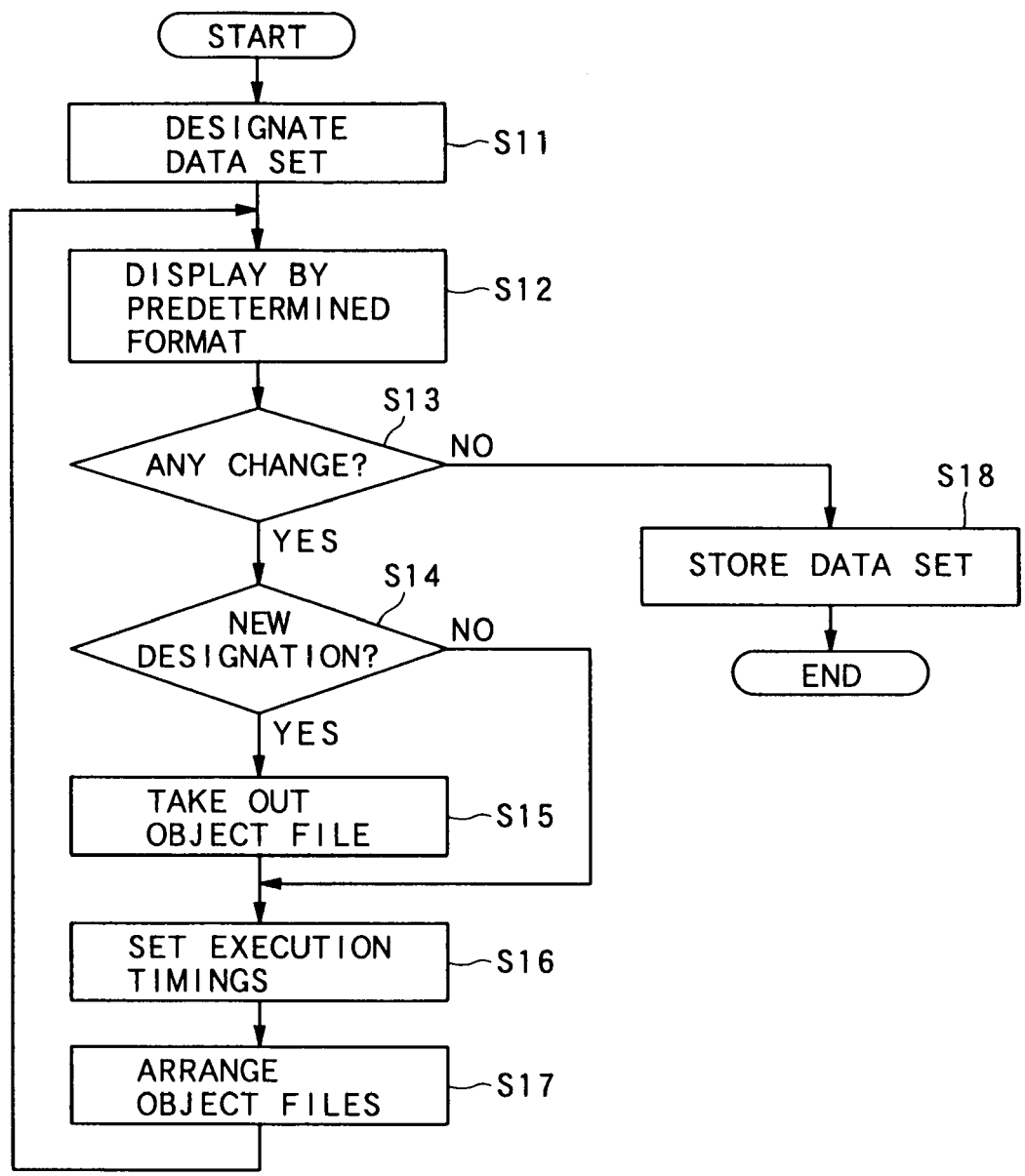
FIG. 9 is a flow chart showing an operation to change the schedule by using a plurality of object files in the first embodiment.

Next, the operation in case of changing the medical care schedule, which has been once made individually as the standard medical care schedule for respective one of the diseases or for the specific patient, is explained with reference to FIG. 9 and FIG. 10. Here, FIG. 9 is a flow chart showing the operation. FIG. 10 is a conceptional diagram in case of changing the schedule in a condition that the medical care schedule table 10 in FIG. 2 is displayed by use of the plurality of object files 21.

In FIG. 9, when changing the medical care schedule, at first, one data set consisting of a plurality of object files 21 related to the once-made medical care schedule is designated by an input through the input device 3 (step S11). This designation may be performed by designating the patient code, the disease code, the patient attribute code etc., which have been already given to each data set. Then, on the basis of the plurality of medical care data and the execution timing data included in this designated data set, the medical care schedule is displayed on the display device 5 in the predetermined format shown in FIG. 2 or FIG. 3 (step S12). In this example, it is assumed that the medical care schedule table 10 is displayed as shown in an upper portion of FIG. 10.

Next, it is monitored by the process device 4 whether or not the input operation indicating the change of the displayed medical care action and/or execution timing is performed through the input device 3 (e.g., by an input though the input device 3 such as a keyboard or a mouse) (step S13). If there is no input operation indicating the change (step S13: NO), the medical care schedule currently displayed is confirmed by the medical care schedule maker, so that the plurality of object files 21 corresponding to the display content at this stage are stored as one data set into the memory device 2 in correlation with the patient code, the disease code and/or the patient attribute code (step S18), and the process is ended.

On the other hand, if there is an input operation indicating the change (step S13: YES), the operation flow proceeds to a step S14. In this example, it is assumed that, as shown in an upper portion of FIG. 10, the change of types and positions of the medical care actions in the medical care schedule table 10 including the addition and erase thereof are executed. More concretely, as shown in FIG. 10, the execution timing of the medical care action corresponding to the object file 21b is changed from December 14 to December 15 (step S13: YES). In this case, it is judged by the process device 4 whether or not the medical care action which has never been displayed is newly designated (step S14). Then, if there is no new designation i.e., if only the execution timing of the medical care action is changed (step S14: NO), the operation flow proceeds to a step S16. On the other hand, if there is the new designation (step S14: YES), after the object file 21 corresponding to the newly designated medical care action is taken out from the memory device 2 (step S15), the process at the step S16 is performed. In this example, as shown in FIG. 10, there is no new designation, but the change of the execution timing for the medical care action corresponding to the object file 21b is performed (step S14: NO).

In the step S16, at least the relative execution timings of the designated medical care actions on the predetermined time axis are set in accordance with the setting order information 220 respectively included in the object file 21 (refer to FIG. 4) after the change, by the process device 4 (step S16). Then, the object files 21a, 21b, 21c, 21d, 21e, ... are rearranged in the order of the execution timings re-set in the above mentioned manner (step S17). Then, the operation flow returns to the step S12, and each of the medical care data are displayed on the display device 5 in the predetermined format on the basis of the re-set execution timings (step S12). Namely, the medical care schedule table 10 is displayed as in the lower portion of FIG. 10 whose execution timings are updated.

Especially when re-setting the execution timings, the fact that the type and position of the specific medical care action are changed gives a certain influence onto the setting order prescribed by the setting order information 220 (e.g., it may precedently determine the execution timings of the changed medical care action) needless to say the case of additionally designating a new medical care action. Thus, the medical care schedule table 10 which is different from that before the change is displayed on the display device 5 (refer to a lower portion of FIG. 10). More concretely, in this example, along with the movement of the medical care action corresponding to the object file 21b, the execution timings of the medical care actions corresponding to the object files 21a and 21e are changed to be delayed by one day respectively. That is, the execution timing of the medical care action corresponding to the object file 21a which is to be executed after the medical care action corresponding to the object file 21b is changed (delayed) by one day in accordance with the change of the execution timing of this medical care action corresponding to the object file 21b, according to the setting order information included in the object file 21a (which is the before and after relation prescribing data 221 in this case). In the same manner, the execution timing of the medical care action corresponding to the object file 21e which is to be executed after the medical care action corresponding to the object file 21b is changed (delayed) by one day in accordance with the change of the execution timing of this medical care action corresponding to the object file 21b, according to the setting order information included in the object file 21e (which is the before and after relation prescribing data 221 in this case). On the other hand, the change is not applied to the execution timings as for the medical care actions corresponding to the object files 21d and 21c, according to the setting order information 220 included therein.

In this manner, even in a case that the medical care schedule maker such as a medical doctor etc., newly designates a plurality of medical care actions by adding, changing or erasing the medical care action for example with respect to a plurality of medical care actions composing one series of medical care schedule, which have been once made, the execution timings of the medical care actions are automatically re-set according to the setting order information 220 included in the object file 21. Thus, it is not necessary for the medical care schedule maker to perform troublesome operations which require labors and certain time such as operations to shift the execution timings of medical care actions one by one. This is very advantageous.

Especially in the present embodiment, in case that the execution timing of another medical care action composing the medical care schedule together with one medical care action is changed, it is efficiently judged whether or not the execution timing of each of the medical care actions is changed, and if one or more execution timings are judged to be changed, they are speedily and certainly changed automatically. Namely, each of the object files 21 further includes intimation order information for transmitting the change intimation data to intimate or inform the change of the pertinent execution timing with respect to another object file, in case that the execution timing of the medical care data 211 included in respective one of the object files 21 is changed. The process device 4 transmits the change intimation data to another object file 21 according to the intimation order information in case that the execution timing is changed, so as to re-set the execution timing according to the setting order information included in another object file 21. By such a construction, in response to the transmission of the change intimation data according to the intimation order information, the execution timings are re-set according to the setting order information included in another object file 21. Therefore, in case that the execution timing of the medical care action related to just one object file 21 is changed, the execution timings of the medical care actions which compose one series of the medical care schedule together with this are speedily, automatically and chain-reactingly re-set.

Incidentally, in the present embodiment, the display device 5 is constructed to display the medical care data indicating the medical care action whose execution timing is changed among the medical care actions after the change, in a display manner different from the medical care data indicating the medical care action whose execution timing is unchanged. Here, "different display manners" means displays different in colors, brightnesses, densities or the like from each other. For example, the changed one (i.e., the medical care data corresponding to the object files 21*a* and 21*e* in FIG. 10) is displayed in a red character or high brightness, while the unchanged one (i.e., the medical care data corresponding to the object files 21*d* and 21*c* in FIG. 10) is displayed in a black character or low brightness. Therefore, the medical care schedule maker can surely recognize and confirm on the display picture plane the medical care data 211 indicating the medical care action, whose execution timing is automatically set and whose execution timing is changed in accompaniment with the changing operation by the input device 3. Alternatively or additionally, a predetermined mark indicating "the change of the execution timing" may be appended to the displayed medical care data on the picture plane.

Especially in the present embodiment, the process device 4 generates the execution timing data indicating the set execution timings with respect to the corresponding object files 21 respectively when setting the execution timings. Each of the object files 21 is adapted to store the generated execution timing data. Then, upon making the medical care schedule later, the medical care data 211 are displayed by the display device 5 in the format of the medical care schedule table 10 shown in FIG. 2 or the medical care schedule list 110 shown in FIG. 3, on the basis of the execution timings indicated by the execution timing data stored in the object file 21, in addition to or in place of the execution timings set by the process device 4. At this time, in case that there already exist the execution timing data in each of the object files 21, it is performed to update the storage content of the object file 21 by the execution timing data indicating the newly set execution timing. Namely, the newest medical care schedule can be displayed on the basis of the execution timing data stored in each of the object files 21.

Therefore, if the operation of setting the execution timing is performed once, as long as there is no change in the medical care schedule, it is possible to display the medical care data by the display device 5 on the basis of the execution timing data stored in each of the object files 21 as they are, which is convenient. Further, even in case that the change is applied to the medical care schedule in the above mentioned manner, it is possible to display the medical care data by the display device 5 at first on the basis of the execution timing data stored in the object file 21, which have been once set by the previous setting operation, and after that, it is possible to easily apply the change to the once-made medical care schedule on this display picture plane, which is also convenient.

From this point of view, the present embodiment may be further constructed to store the data set of a plurality of object files including a plurality of medical care data indicating a plurality of medical care actions composing one series of medical care schedule into the memory device 2 in correlation with the patient code assigned to each individual patient (e.g., a numerical value code in predetermined digits). Alternatively, the present embodiment may be constructed to store each data set into the memory device 2 in correlation with the disease code (e.g., a numerical value code in predetermined digits) assigned to each individual disease among a plural kinds of diseases (e.g., angnapctori, pneumonitis, stomach cancer, cerebral infarction). Alternatively, the present embodiment may be constructed to store each data set into the memory device 2 in correlation with the patient attribute code (e.g., a numerical value code in predetermined digits) assigned to each individual patient attribute in advance including the cardinal symptom (e.g., sex, age, body property, as well as the cardinal symptom). And it is preferable that, after that, the data set corresponding to the designated code is designated by designating the patient code, the disease code or patient attribute code by the input device 3.

In this manner, since each data set is stored in the memory device 2 in correlation with the patient code, the disease code or patient attribute code, it is possible to easily display the medical care schedule by the display device 5 without setting the execution timing again, on the basis of the medical care data 211 and the execution timing data included in the data set corresponding to the designated patient code, disease code or patient attribute code, just by designating the patient code, the disease code or the patient attribute code. As a result, by making the medical care schedule once as for an arbitrary patient, it is possible to read out the medical care schedule for the patient from the memory device 2 and easily and speedily display it, by designating the patient code, so that the operation of changing the schedule can be also speedily performed. By making the medical care schedule once as for an arbitrary disease, it is possible to read out the medical care schedule for the disease from the memory device 2 and easily and speedily display it, by designating the disease code, so that the operation of changing the schedule can be also speedily performed. Further, by making the medical care schedule once as for an arbitrary patient attribute, it is possible to read out the medical care schedule for the patient attribute from the memory device 2 and easily and speedily display it, by designating the patient attribute code, so that the operation of changing the schedule can be also speedily performed.

The standard medical care schedule corresponding to each disease (each disease code) or the standard medical care schedule corresponding to each patient attribute (each patient attribute code) as described above has a high flexibility as a source for making the medical care schedule for a specific patient. Thus, the data set indicating the standard medical care schedule corresponding to each disease (each disease code) or the standard medical care schedule corresponding to each patient attribute (each patient attribute code) may be stored in advance in the record medium 8a together with the computer program, and may be loaded together when the computer program is loaded. Alternatively, a large number of data sets respectively indicating the standard medical care schedules corresponding to almost all of diseases (almost all of disease codes) and/or the standard medical care schedules corresponding to almost all of patient attributes (almost all of patient attribute codes) mat be stored in advance in a large size memory device equipped in a separate computer system, and the aiding system 1 may download the data set corresponding to a desired disease code or patient code through the communication device 7 (refer to FIG. 1), from this separate computer system having the large size memory device and a communication device.

In the above explained first embodiment, the table format shown in FIG. 2 and the list format shown in FIG. 3 are adapted as the predetermined format to display the medical care schedule. It is possible to select one of these formats and switching these format to each other by a command input through the input device 3. Especially, it is convenient to switch the picture plane for the medical care schedule table 10 of FIG. 2 to the picture plane for the medical care schedule list 110 of FIG. 3 by an execution of a predetermined command while positioning the cursor on a specific date on the medical care schedule table 10.

It is also possible naturally to display the medical care data by a predetermined format other than the formats exemplified in FIG. 2 and FIG. 3. The meaning of the format to arrange "in an order of execution" in the present invention is so wide to include all of the formats in which the medical care actions are arranged in the order of execution, at least partially in any sense, with respect to an arbitrary spatial or temporal axis such as a spatially vertical, horizontal, oblique or forward-backward axis, or a temporally before and after axis and the like.

In the above explained embodiment, as shown in FIG. 4, various kinds of informations such as the past performance information 230, the order information 240, the execution timing data 260 etc., in addition to the medical care data 211 and the setting order information 220 are stored in each of the object files 21. However, as long as the object file 21 stores at least the medical care data 211 and the setting order information 220, it is possible to exert the function of automatically setting the execution timings of each medical care action by a unit of the object file 21. Thus, it is possible not to store the information other than those in the object file 21.

(II) Modified Examples of Medical Care Schedule Table

FIG. 11 shows another example of the table which can be outputted by the display device 5 and the printer 6 in the present embodiment. In this case, the process device 4 is adapted to set the timing including the date and the time as for the execution timing data at least partially, and the memory device 2 is adapted to store the execution timing data indicating the time in addition to the date. Then, each medical care action is displayed in respective one of cells 20a in the medical care schedule table 20 such that they are further arranged for each of the set time of one day. By this, in a case where many medical care actions to be scheduled and recorded exist in one day such as the day in the hospitalization for example, since the medical care actions are arranged in each cell 20 (frame) of the table for each time of one day, it is easy to visually recognize the medical care actions performed in one day, which is very convenient.

Figure 12:
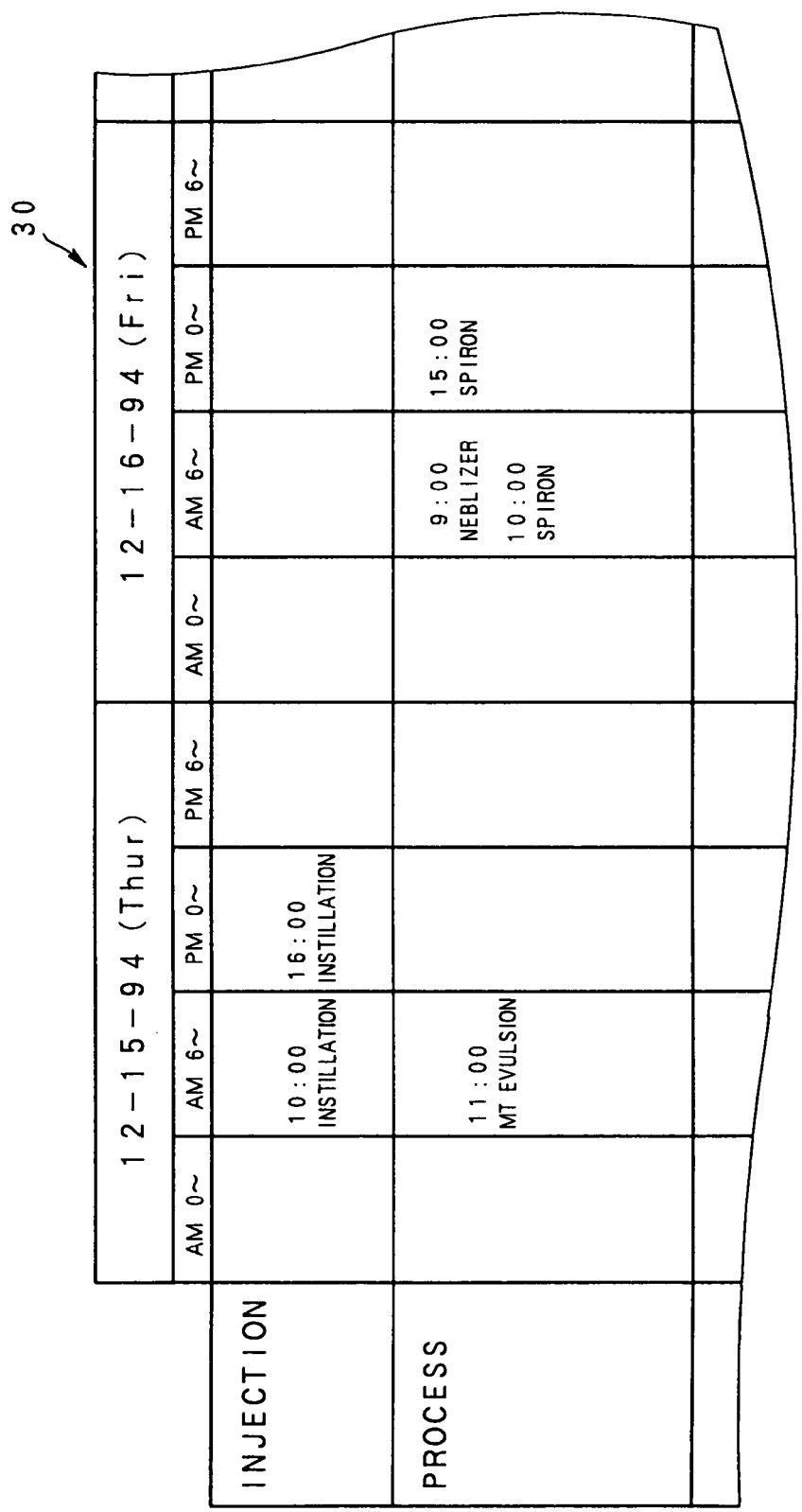
FIG. 12 is a plan view showing another example of a table which is graphically outputted by the first embodiment.

FIG. 12 shows another example of the table which can be outputted by the display device 5 and the printer 6 in the present embodiment. In this case, the process device 4 is adapted to set the timing including the date and time as for the execution timing data at least partially, and the memory device 2 is adapted to store the execution timing data indicating the time in addition to the date. Then, the medical care data at least partially in the medical care schedule table 30 are outputted with being arranged for each predetermined time unit instead of each date. More concretely, the medical care schedule table 30 is outputted in which the medical care actions in each 6 hours are put in one frame of the table and the columns are arranged every 6 hours. By this, if it is the case where a lot of medical care actions are to be recorded or scheduled such as the day in the hospitalization, a fine schedule for each time can be scheduled and recorded. Other than 6 hours, although a unit such as 1, 2, 3, 4, 8 or 12 hours which can easily divide 24 hours (one day) can be preferably used here, an arbitrary time unit can be used such that a time unit of long time length may be used with respect to the day time while a time unit of short time length may be used with respect to the night time. By graphically outputting the table 30 having the arrangement in the time unit, it is easy to visually recognize the medical care actions performed in one day, which is convenient.

Figures 13, 14:
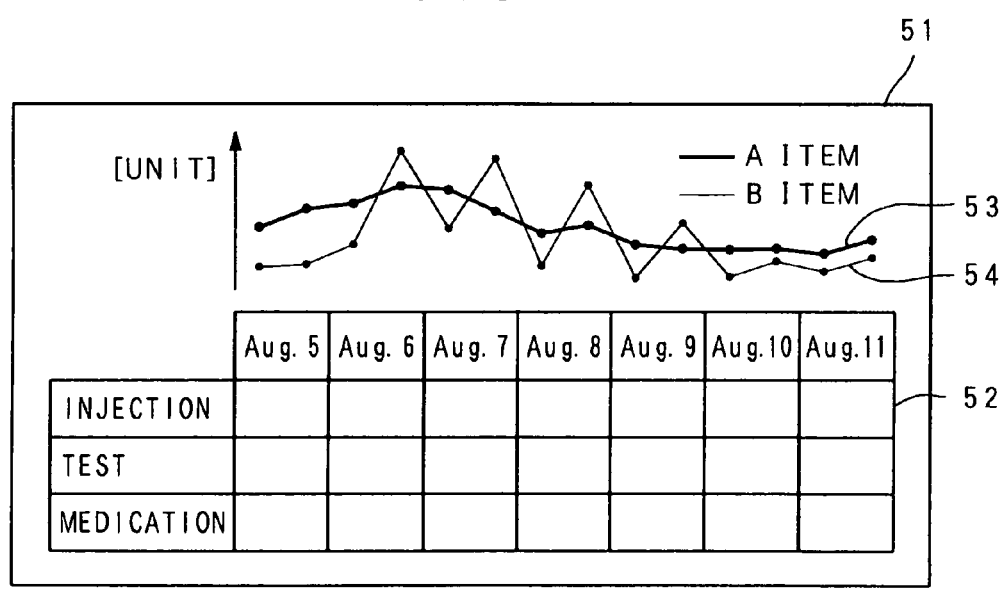
FIG. 13 is a plan view showing another example of a table which is graphically outputted by the first embodiment.
FIG. 14 is a plan view showing another example of a table which is graphically outputted by the first embodiment.

FIG. 13 shows another example of the table which can be outputted by the display device 5 and the printer 6 in the present embodiment. In this case, the medical care data at least partially in the medical care schedule table 40 are outputted in a format of a table in which the medical care data are integrated by a unit of a plurality of successive dates instead of arranging them for each date. More concretely, the table 40, in which the medical care actions in each one month period are put in one frame 41 of the table and the columns are arranged ever month is outputted. Other than one month, although a time unit such as 3 days, one week, one year or 10 years which are easily understood, can be preferably used here, an arbitrary time unit can be used such that a short time length may be used for the time unit with respect to the period of the hospitalization while a long time length may be used for the time unit with respect to the period for the outpatient. By prescribing the size of each cell in correspondence with the amount of the medical care actions, it is easy to visually recognize the aspect of the medical care actions in a long time span, which is convenient.

FIG. 14 shows another example of the table which can be outputted by the display device 5 and the printer 6 in the present embodiment. In this case, the reference information data 214 (refer to FIG. 4), which indicate the detail of the predetermined medical care action, such as numerical data related to a certain medical care action which is repeatedly recorded with respect to a plurality of dates (e.g. the body temperature data, the blood pressure data, the specific content concentration in the blood data measured for each day), are correlated with the medical care data. Then, the table 52 is displayed at one portion of the picture plane 51 of the display device 5 and at the same time the numerical data is displayed as a graph having the abscissa corresponding to the arrangement of the dates of the table 52 at another portion of the picture plane 51. Namely, as shown in FIG. 14, the table 52 is displayed in the lower portion of the picture plane 51 while a polygonal line graph 53 indicating the numerical data as for the A item (e.g. the body temperature) and the polygonal line graph 54 indicating the numerical data as for the B item (e.g. blood pressure), each of which have the time axis of the date of the table 52, are displayed in the upper margin of the table 52. Accordingly, since the numerical data can be shown as the graph in correspondence with the date of the table 52, it is easy to visually recognize the relationship between the medical care actions which have been performed in the past and the numerical data which indicate the body condition etc. of the patient to which the medical care actions were applied. As shown in the example of FIG. 14, if there are several data obtained by the measurements several times in one day, by drawing the graph such that the width of each frame of the table 52, which expresses one day, is converted to 24 hours, and that the upper line of the table 52 is made corresponding to the time axis of the graph, the time relationship between the numerical data and the table 52 can be still easily recognized. On the other hand, even if the numerical data do not always exist for every date, it is still possible to draw the polygonal line graph by use of the existing data and/or by interpolating the existing data.

The above explained modified examples of the medical care schedule table can be applied to not only the first embodiment but also other embodiments described below.

(III) Second Embodiment

The second embodiment of the present invention is explained with reference to FIG. 15 to FIG. 18.

In the first embodiment, there is such a premise that the plurality of medical care actions composing one series of medical care schedule have properties which are not contradict to each other, and that all of the medical care actions composing one series of the medical care schedule are basically performed. In the actual medical care field however, there may rather often happen such an event that it is difficult to determine the diagnosis and what to perform next is changed drastically depending upon a result of a previous action. Accordingly, in the second embodiment, one series of medical care schedule is constructed by a plurality of medical care action candidates each of which has a probability to be disjunctively performed in the future, instead of or in addition to the scheduled medical care actions which are to be certainly performed in the future in the first embodiment. Here, to "disjunctively perform" means to really perform either one of them (but not both of them). The hardware structure of the second embodiment is same as that of the first embodiment (refer to FIG. 1), and the logical structure of the object file 21 is also similar as that of the first embodiment (refer to FIG. 4).

In the second embodiment, a plurality of medical care action candidates, one of which is to be disjunctively performed, are designated instead of or in addition to the medical care actions to be performed in the future in the first embodiment, by the input device 3 or the like. Then, at least the relative execution timing candidates of the designated medical care action candidates are set, instead of or in addition to the execution timings, according to the setting order information 220, by the process device 4. Then, the medical care data 211 respectively indicating the medical care action candidates are displayed in a predetermined format by the display device 5 instead of or in addition to the medical care data respectively indicating the medical care actions, on the basis of the set execution timing candidates. Thus, in case that there exist various types of medical care actions, each of which has a probability to be performed in the future in accordance with the disease etc., since the disease, illness or the like is unknown e.g., at an initial stage of the medical care schedule such as before the diagnosis is determined, it is very convenient to make the medical care schedule.

Figure 15:
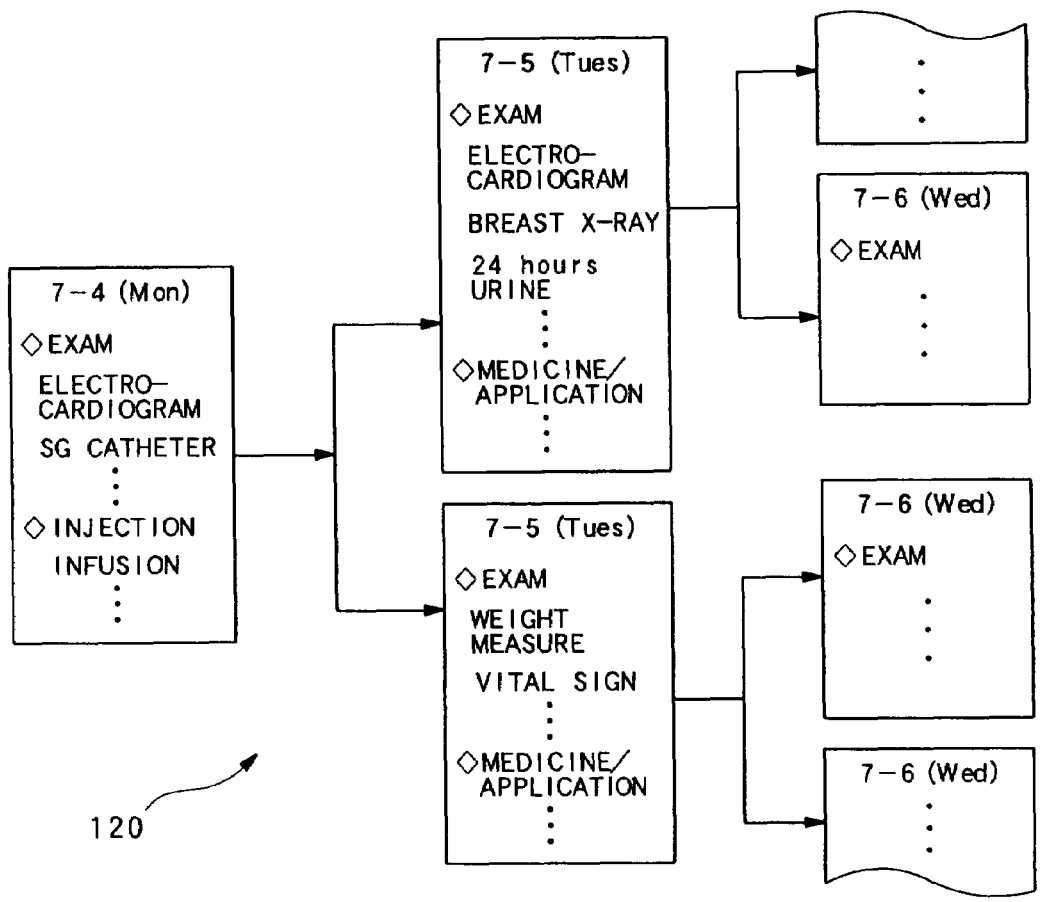
FIG. 15 is a plan view showing one example of a decision tree which is graphically-outputted by a second embodiment of the present invention.
Figure 16:
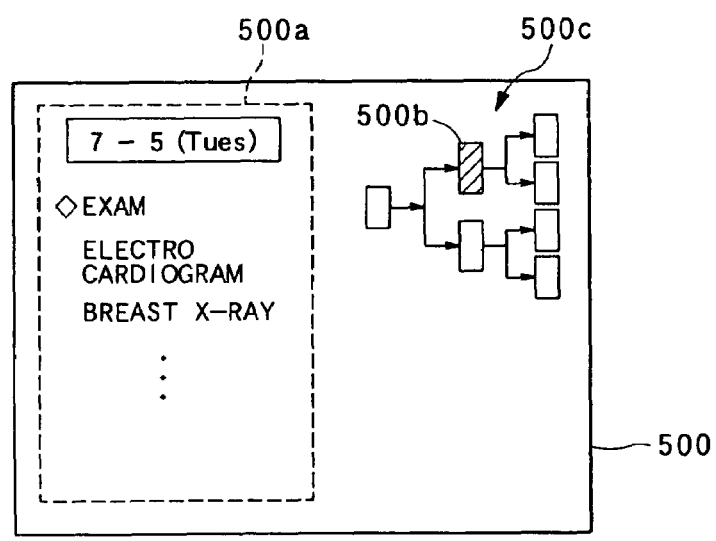
FIG. 16 is a plan view showing another example of a decision tree which is graphically-outputted by the second embodiment.

In the second embodiment, as shown in FIG. 15, the predetermined format for displaying the medical care data may be such a format of a decision tree 120 in which the plurality of medical care action candidates to be disjunctively performed are arranged in the order of the execution timing candidates (which is the order of the date in the example of FIG. 15) for example. In this case, it is possible to perform an automatic setting of the execution timing of each medical care action candidate on this decision tree 120 while displaying the decision tree 120 indicating as a node (divergence) the fact that there are a plurality of candidates. In this case, the actual display picture plane may be adapted to allow a magnified display of a desirable portion while scrolling the decision tree 120 itself in the up and down direction and/or the left and right direction. Alternatively, as shown in FIG. 16, each portion 500a corresponding to respective date of the list 110 shown in FIG. 3 may be displayed on a display picture plane 500 of the display device 4 while a location master 500c, which indicates each position 500b on the scale-reduced and displayed decision tree 120, may be displayed.

Next, the operation of automatically setting the execution timings and the operation of displaying the medical care schedule based on the result of the setting in the system for aiding to make the medical care schedule in the second embodiment constructed in the above described manner, are explained.

At first, the operation of newly making the medical care schedule composed of various data included in the plurality of object files 21 are explained with reference to FIG. 17. Here, FIG. 17 is a conceptional diagram in case that the decision tree 120 in FIG. 15 is made and displayed by use of the plurality of object files 21.

Figure 17:
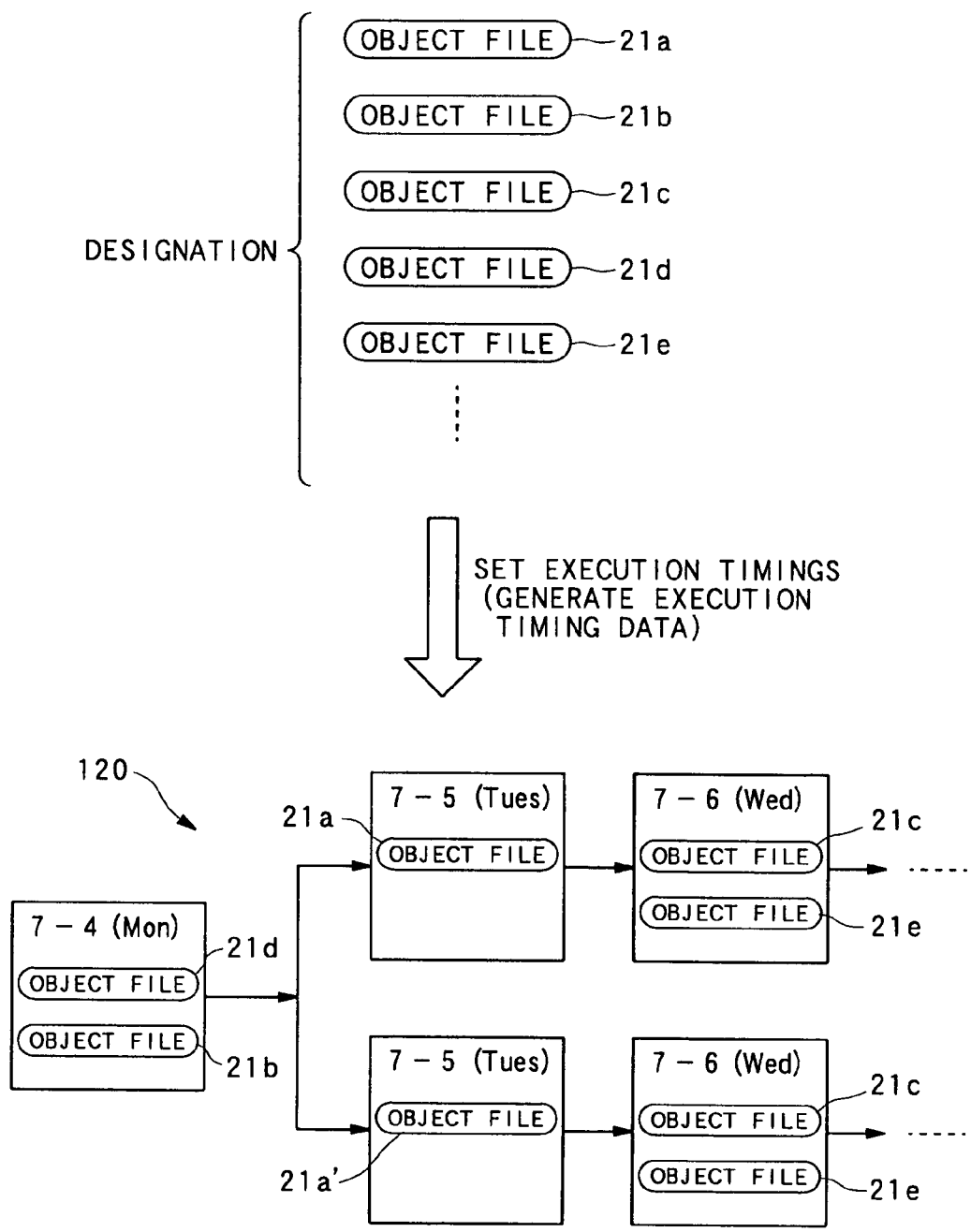
FIG. 17 is a conceptional diagram of an operation to construct and display the decision tree of FIG. 15 by using a plurality of object files in the second embodiment.

In FIG. 17, when making the medical care schedule, at first, a plurality of medical care action candidates composing one series of medical care schedule are designated one by one by an inputting operation through the input device 3 such as a keyboard, a mouse and the like (refer to FIG. 1), or are designated at once by an inputting operation through the memory device 2 or the reading device 1 such as a hard disc, a floppy disk and the like (refer to FIG. 1). Then, a plurality of object files 21a, 21b, 21c, 21d, 21e, . . . corresponding to the designated medical care action candidates are taken out from the memory device 2, by the process device 4 (refer to FIG. 1). Then, at least the relative execution timing candidates of the designated medical care action candidates on the predetermined time axis are set in accordance with the setting order information 220 respectively included in the object file 21 (refer to FIG. 4), by the process device 4. Then, when the execution timing candidates are set in this manner, the object files 21 are respectively made into the object files 21a, 21b, 21c, 21d, 21e, . . . which are arranged in correspondence with the data filling each block of the decision tree 120 shown in FIG. 15, according to the types of the medical care action candidates and the set execution timing candidates for example (refer to a lower portion of FIG. 17).

Next, the operation in case of changing the medical care schedule, which has been once made individually as the standard medical care schedule for respective one of the diseases or for the specific patient, is explained with reference to FIG. 18. Here, FIG. 18 is a conceptional diagram in case of changing the schedule in a condition that the decision tree 120 in FIG. 15 is displayed by use of the plurality of object files 21.

In FIG. 18, when changing the medical care schedule, at first, the change of the type and/or position of the medical care action candidate (refer to an upper portion of FIG. 18) including the addition and the erasure is performed through an input of the input device 3 such as a keyboard, a mouse etc., by the medical care schedule maker such as a medical doctor. More concretely in this example, it is assumed that the execution timing candidate of the medical care action candidate corresponding to the pertinent object file 21b is changed from July $4^{th}$ to July $5^{th}$. Then, at least the relative execution timings of the designated medical care action candidates on the predetermined time axis are set in accordance with the setting order information 220 respectively included in the object file 21 (refer to FIG. 4) after the change, by the process device 4. At this time, the fact that the type and position of the specific medical care action candidate are changed gives a certain influence onto the setting order prescribed by the setting order information 220 (e.g., it may precedently determine the execution timings of the changed medical care action) needless to say the case of additionally designating a new medical care action. Thus, the decision tree 120 which is different from that before the change is displayed on the display device 5 (refer to a lower portion of FIG. 18). More concretely, in this example, along with the movement of the medical care action candidate corresponding to the object file 21b, the execution timings of the medical care action candidates corresponding to the object files 21a and 21a' are changed to be delayed by a few hours respectively (the date is not changed respectively). That is, the execution timing is changed (delayed) according to the setting order information 220 included in the object files 21a and 21a'. On the other hand, the change is not applied to the execution timing candidates as for the medical care action candidates corresponding to the object files 21d and 21c, according to the setting order information 220 included therein. Further, the execution timing of the object file 21e is also changed (delayed) to the next day according to the setting order information 220 included therein.

In this manner, even in a case that the medical care schedule maker such as a medical doctor etc., newly designates a plurality of medical care action candidates by adding, changing or erasing the medical care action candidate for example with respect to a plurality of medical care action candidates composing one series of medical care schedule, which have been once made, the execution timing candidates of the medical care action candidates are automatically re-set according to the setting order information 220 included in the object file 21. Thus, it is not necessary for the medical care schedule maker to perform troublesome operations which require labors and certain time such as operations to shift the execution timing candidates of medical care action candidates one by one. This is very advantageous.

Incidentally, in the second embodiment, the execution timing data indicating the once-set execution timing candidate may be stored in respective one of the object files 21, in the same manner as the first embodiment. Further, the data set of a plurality of object files 21 corresponding to one series of medical care schedule may be stored in the memory device 2 in correlation with the patient code, the disease code and/or the patient attribute code. Furthermore, the structure to display the changed medical care action in a format other than the table, the structure to generate and store the execution timing data for the changed medical care action, the structure to update the content of the memory device 2 by the generated execution timing data and so forth in the first embodiment can be adapted to the second embodiment in the same manner as the first embodiment.

In the above described embodiments, the input device 3 may be preferably adapted to designate at least the date for at least one medical care action among the medical care actions scheduled to be performed in the future, and the process device 4 may be preferably adapted to set a plurality of execution timings by at least the unit of date on the basis of the date designated by the input device 3. In this case, each execution timing is set by an absolute time unit such as X year, Y month, Z date, and that the display on the display device 5 is also performed by the unit of date which is the absolute time unit. Especially, just by designating the date (i.e., the absolute time) for the medical care action, which is the "medical operation" as a most important item in the schedule for example, the other schedules for other items can be automatically set, which is convenient.

In the above described embodiments, there may be further equipped an alarm device for generating an alarm in case that a plurality of execution timings set according to the setting order information 220 are contradict to each other or in case that the execution timings which are not contradict to each other cannot be set. Such an alarm device may be constructed to display an alarm message indicative of "impossible to set the execution timing" on the picture plane of the display device 5, or to generate a voice alarm indicative of the alarm message through a speaker equipped in the aiding system 1. In this case, when a medical care schedule, which is not actually possible, is to be nearly made by the automatic setting according to the setting order information 220, the medical care schedule maker can speedily recognize the fact.

The aiding system 1 in each of the embodiments may be provided with a timer or counter for counting the date, and the display data may be generated such that the graphically outputted portion related to the date coincident with "today" is displayed in a manner different from the other graphically outputted portion, on the basis of the date counted by the timer or counter. Here, as the display and/or print in a different manner, there are display methods of displaying or printing the image different in the brightness, the color, the style, the kind of lines, the concentration, the half-tone dot meshing etc. on the picture plane or the printed sheet. Alternatively or additionally, a predetermined mark indicating "today" may be appended to the column for the corresponding date.

(IV) Third Embodiment

A third embodiment of the present invention is explained with reference to FIG. 19.

Figure 19:
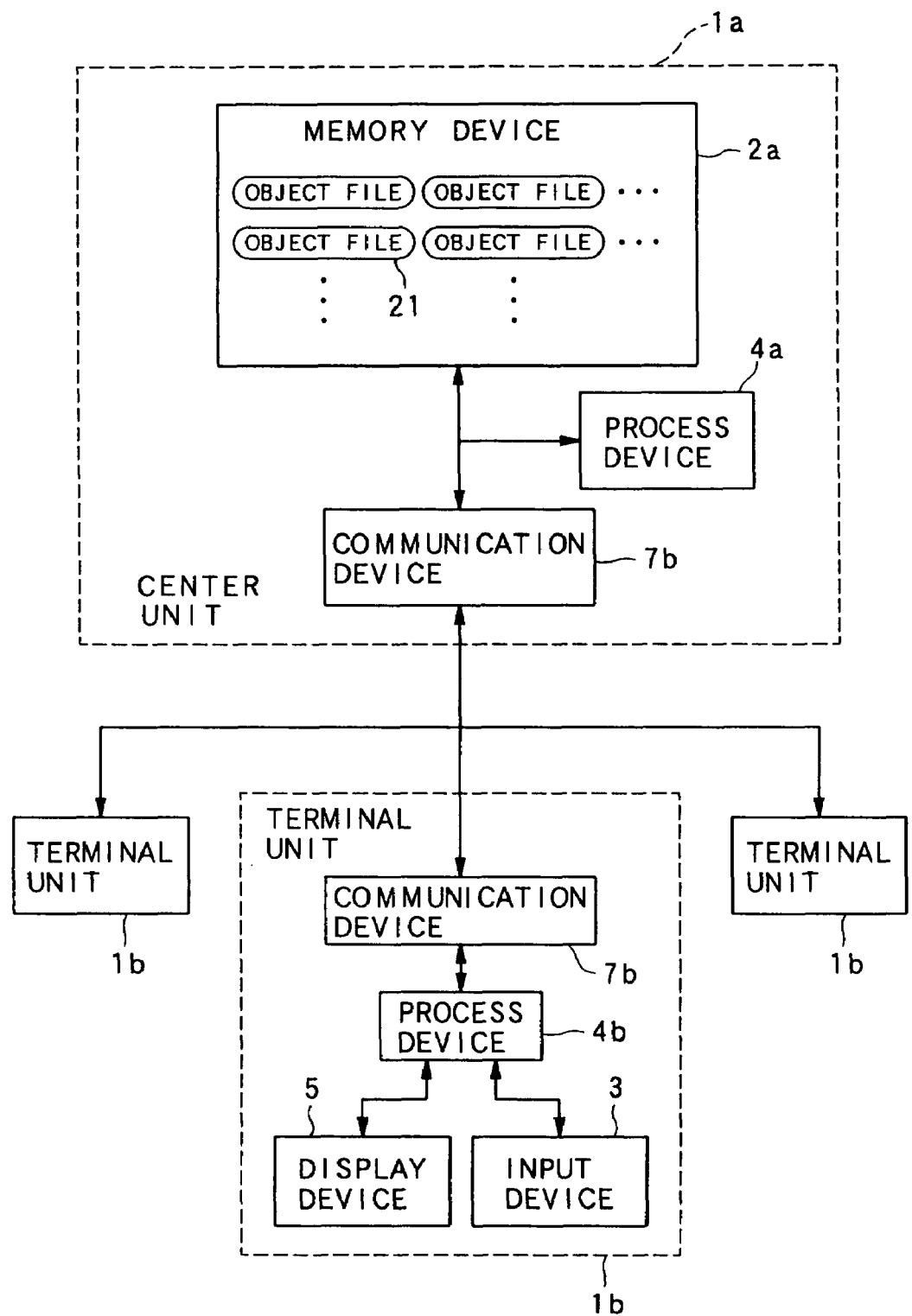
FIG. 19 is a block diagram of a system for aiding to make a medical care schedule as a third embodiment of the present invention.

In FIG. 19, the system for aiding to make the medical care schedule as the third embodiment is provided with a plurality of units communicated through the transmission line. A plurality of object files 21 are provided on the side of a center unit 1a, while the input device 3, the process device 4, the display device 5 and the communication device 7 are provided on the side of each terminal unit 1b. The center unit 1a is provided with: a large size computer, a host computer or a server; and a large size memory device 2a for storing the object files 21. The terminal unit 1b is provided with a personal computer, a work station, a mobile computer (i.e., a hand carry type information terminal), an electronic diary or the like. Further, (i) the object files 21 stored in the memory device 2a of the center unit 1a and (ii) the input device 3, the process device 4 and the display device 5 provided on the terminal unit 1b are coupled through a communication line, which may be a wire-line, a wireless-line, an exclusive line, a general line, a telephone line or the like. Therefore, by virtue of such a structure that the plurality of object files 21 are stored in the large size memory device 2a equipped on the center unit 1a and that a plurality of terminal units 1b are arranged, it is possible to commonly use the same data by a plurality of terminal units 1b. In such a structure, the process device 4 may be equipped on the center unit 1a or the terminal unit 1b. According to the present embodiment, a plurality of object files 21 or data sets stored in the memory device 2a of the center unit 1a can be commonly used, and it is not necessary to equip a large size memory device, which has a capacity enough to store a large number of object files 21, on each terminal unit 1b, which is advantageous in a practical sense.

(V) Fourth Embodiment

A fourth embodiment of the present invention is explained with reference to FIG. 20.

In the above first to third embodiments, it is sometimes difficult to categorize the type of the medical care action. Namely, one action may be categorized into either one of a type A and a type B. Further, one action may be categorized into a type A and may be categorized into a type A', which includes the type A or is included in the type A, depending upon the types composing the medical care schedule table, which may be set as a default one or which may be selected or modified by the medical care schedule maker.

Therefore, in the fourth embodiment, as shown in an upper portion of FIG. 20, the object files 21a, 21b, 21c, 21d, . . . have multiple correlation information 301a, 301b, 301c, 301d, . . . , respectively. Thus, depending on the types present in the medical care schedule table 10 shown in FIG. 2, each of the object files 21a, 21b, 21c, 21d, . . . finds out to which type the pertinent object file itself is to be corresponding, with referring to the corresponding type data and the priority order data in each multiple correlation information 301. For example, as shown in the upper portion of FIG. 20, the multiple correlation information 301a of the object file 21a has the corresponding type data and the priority order data indicating that the object file 301a is to belong to the type "oral medicine" with the highest priority (priority No. 1), is to belong to the type "medicine" with the second priority (priority No. 2), is to belong to the type "treatment" with the third priority (priority No. 3) and so on. The multiple correlation information 301b of the object file 21b has the corresponding type data and the priority order data indicating that the object file 301b is to belong to the type "injection" with the highest priority, is to belong to the type "medicine" with the second priority, is to belong to the type "treatment" with the third priority and so on. The multiple correlation information 301c of the object file 21c has the corresponding type data and the priority order data indicating that the object file 301c is to belong to the type "workup test" with the highest priority, is to belong to the type "test" with the second priority, is to belong to the type "examination" with the third priority and so on. The multiple correlation information 301d of the object file 21d has the corresponding type data and the priority order data indicating that the object file 301d is to belong to the type "daily test" with the highest priority, is to belong to the type "test" with the second priority, is to belong to the type "measure" with the third priority and so on.

Accordingly, in case that a medical care schedule table 10a shown in a lower left portion of FIG. 20 is currently displayed, i.e., the types "oral medicine", "injection" and "test" are present in the type column of the medical care schedule table 10a, the object file 21a is correlated with the "oral medicine" type according to the priority order data of the multiple correlation information 301a (indicating that the highest priority is given to the "oral medicine"). In this case, the object file 21b is correlated with the "injection" type according to the priority order data of the multiple correlation information 301b (indicating that the highest priority is given to the "injection"). In this case, the object file 21c is correlated with the "test" type according to the priority order data of the multiple correlation information 301c (indicating that the second priority is given to the "test") while the "workup test" type to which the highest priority is given by the multiple correlation information 301c is not present in the table 10a. Further in this case, the object file 21d is correlated with the "test" type according to the priority order data of the multiple correlation information 301d (indicating that the second priority is given to the "test") while the "daily test" type to which the highest priority is given by the multiple correlation information 301d is not present in the table 10a.

On the other hand, in case that a medical care schedule table 10b shown in a lower right portion of FIG. 20 is currently displayed, i.e., the types "medicine", "workup test" and "daily test" are present in the type column of the medical care schedule table 10b, the object file 21a is correlated with the "medicine" type according to the priority order data of the multiple correlation information 301a. In this case, the object file 21b is correlated with the "medicine" type according to the priority order data of the multiple correlation information 301b. In this case, the object file 21c is correlated with the "workup test" type according to the priority order data of the multiple correlation information 301c. Further in this case, the object file 21d is correlated with the "daily test" type according to the priority order data of the multiple correlation information 301d.

In this manner, according to the fourth embodiment, it is possible to correlate respective one of the object files 21a, 21b, 21c, 21d, . . . , to the appropriate type on the basis of the multiple correlation information 301a, 301b, 301c, 301d, . . . , even in case that the types present in the table are not fixed but are changed in various manners in favor of the medical care schedule maker such as a doctor.

In addition, if there exists any object file which cannot find to which type the object file itself is to belong, an error message indicating the fact may be outputted. Alternatively, the present embodiment may be constructed such that an operation of automatically re-formatting the table to make a room (i.e., a new type column) for the pertinent object file in the currently displayed table may be performed according to the multiple correlation information of the object files.

Furthermore, the present embodiment may be constructed such that an operation of automatically re-formatting the table to omit or thin out a row for a type, with which any one of the object files is not correlated, in the currently displayed table is performed according to the multiple correlation information 301 (refer to FIG. 20) or the medical care data 211 (refer to FIG. 4) of the object files 21.

Namely, as shown in an upper portion of FIG. 21, if an empty row exists (i.e., each of the row for the "injection" and the row for the "rehabilitation" is empty) in the table 10, the empty row is thinned out by the automatic re-formatting operation according to the object file 21, so that a medical care schedule table 10' in which no empty row exists is displayed as shown in a lower portion of FIG. 21. Thus, it is possible to efficiently see the table 10' within a limited vision of the display device.

In the same manner, if an empty column exists in the table 10, the empty column may be thinned out by the automatic re-formatting operation according to the object file 21, so that the medical care schedule table in which no empty column exists may be displayed.

(VI) Function of System

Finally, the functions of the system for aiding to make the medical care schedule used in the above described embodiments are conceptually indicated in FIG. 22.

In FIG. 22, the function of the aiding system 1 unifies: a function of "operation on the picture plane" 13 realized by the display device 5, the input device 3 etc. shown in FIG. 1; a function of "display" 14 realized by the display device 5 etc., a function of "various system interface" 15 realized by the communication device 7, the control device 4 etc. The function of "operation on the picture plane" 13 unifies a function of "new input" 13a, a function of "add/modify input" 13b and a function of "delete" 13c. The function of "display" 14 unifies a function of "displaying the table" 14a by use of the medical care data in the predetermined format (refer to FIG. 2, FIG. 3 and FIG. 15), a function of "displaying the result" 14b by use of the medical care data and/or the detail medical data, a function of "displaying the graph" 14c for displaying the graph by use of the detail medical data, and a function of "magnification change" 14d for changing the magnification of picture plane of the display device 5.

Further, the function of "various system interfaces" 15 unifies a function of "various order" 15a for sending an order between each medical care navigation units, a function of "electronic clinical chart" 15b used by the operation unit in medical examination, and a function of "medical account" 15c used in the operation unit for account. The various order function 15a is used in a terminal unit for medicine, which is constructed to graphically-output a medicine list after receiving a medicine order through a communication device from each system interface e.g., from a clinical division. In the present embodiments, on the basis of the order information included in each of the object files 21 (refer to FIG. 4), it is possible to speedily issue the order corresponding to each medical care action.

The electronic clinical chart function 15b is used in a terminal unit for clinic, which is constructed to graphically-output the clinic chart by use of various data received through the communication device from each system interface. The medical account function 15c is used in a terminal unit for accounting which is constructed to perform a calculation for the medical account by use of various data received through the communication device from each system interface and to graphically-output the medical account book on the basis of the result of calculation.

In this manner, since the functions are unified in the multiple layered structure, each function can be efficiently called and mutual functions organically combined to each other can be performed by the aiding system 1, which is convenient.

As described above in detail, according to each of the present embodiments, a system for aiding to make the medical care schedule can be realized, which can aid a medical care schedule maker such as a medical doctor etc., to easily and speedily make an appropriate medical care schedule.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 10-210496 filed on Jul. 27, 1998 including the specification, claims, drawings and summary is incorporated herein by reference in its entirety.

What is claimed is:

1. A system for aiding to make a medical care schedule by determining at least an execution order of a plurality of medical care actions which compose a treatment procedure sequence for a treatment of a particular patient, the system comprising:
    a plurality of object files set in advance, wherein the plurality of object files are divided into a plurality of data sets according to categories associated with diseases, wherein a different disease code is assigned to each of the data sets respectively, each object file including:
        (i) medical care data indicating one of a plurality of medical care actions set in advance, and
        (ii) setting order information indicating at least a position of execution of one of the plurality of medical care actions in relation to the plurality of other medical care actions;
    an input device for designating the plurality of medical care actions which compose the treatment procedure sequence for the treatment of the particular patient, wherein the input device is further adapted to designate a disease code and to identify a data set corresponding to the designated disease code;
    a process device for selecting a plurality of particular object files that respectively include the medical care data indicating the designated plurality of medical care actions from among the plurality of object files set in advance, and determining an execution order of the designated plurality of medical care actions in accordance with the position of execution of each of the designated plurality of medical care actions indicated by the setting order information of each of the selected plurality of particular object files and based on the plurality of object files included in the identified data set; and
    a display device for displaying the execution order of the designated plurality of medical care actions determined by the process device.

2. A system according to claim 1, wherein
    the plurality of object files are further divided into a plurality of patient attribute data sets according to categories associated with patient attributes including at least a cardinal symptom, wherein each patient attribute data set is assigned a different patient attribute code,
    the input device is further adapted to designate a patient attribute code and to identify a data set corresponding to the designated patient attribute code, and
    the process device determines the execution order of the designated plurality of medical care actions based on the plurality of object files included in the identified data set corresponding to the designated patient attribute code.

3. A system for making a medical care schedule by generating at least two execution orders of a plurality of medical care action candidates, which compose treatment procedure sequence candidates for treating a patient, the system comprising:
- a plurality of object files set in advance, wherein the plurality of object files are divided into a plurality of data sets according to categories associated with diseases, wherein a different disease code is assigned to each of the data sets respectively, each object file including:
  (i) medical care data indicating one of a plurality of medical care action candidates set in advance, and
  (ii) setting order information indicating at least a position of execution of said one of the plurality of medical care action candidates in relation to the plurality of other medical care action candidates;
- an input device for designating the plurality of medical care action candidates which compose the treatment procedure sequence candidates for treating the patient, wherein the input device is adapted to designate a disease code and to identify the data set corresponding to the designated disease code;
- a process device for selecting a plurality of object files, each object file including the medical care data indicating the designated plurality of medical care action candidates from among the plurality of object files set in advance, and determining the at least two execution orders of the designated plurality of medical care action candidates in accordance with the position of execution of each of the designated plurality of medical care action candidates indicated by the setting order information of each of the selected plurality of particular object files and based on the plurality of object files included in the identified data set; and
- a display device for displaying the at least two execution orders of the designated plurality of medical care action candidates determined by the process device.

4. A computer readable medium having a program of computer readable instructions to be read by a system to perform method processes, said system comprising a plurality of object files, wherein the plurality of object files are divided into a plurality of data sets according to categories associated with diseases, wherein a different disease code is assigned to each of the data sets respectively, each object file including (i) medical care data indicating one of various medical care actions set in advance, and (ii) setting order information indicating at least a position of execution of said one of the various medical care actions among the various medical care actions, said system is used for making a medical care schedule by determining at least an execution order of a plurality of medical care actions which compose a treatment procedure sequence for treating a patient, said method processes comprising:
- designating the plurality of medical care actions that compose the treatment procedure sequence for treating the patient;
- designating a disease code and identifying a data set corresponding to the designated disease code;
- selecting a plurality of particular object files that include the medical care data indicating the designated plurality of medical care actions from among the plurality of object files set in advance;
- determining the execution order of the designated plurality of medical care actions in accordance with the position of execution of each of the designated plurality of medical care actions indicated by the setting order information of each of the selected plurality of particular object files and based on the plurality of object files included in the identified data set; and
- displaying the execution order of the designated plurality of medical care actions.

5. A computer readable medium having a program of computer-readable instructions, to be read by a system to perform method processes, said system comprising: a plurality of object files, wherein the plurality of object files are divided into a plurality of data sets according to categories associated with diseases, wherein a different disease code is assigned to each of the data sets respectively, each object file including (i) medical care data indicating one of a plurality of medical care action candidates set in advance, and (ii) setting order information indicating at least a position of execution of said one of the plurality of medical care action candidates among the plurality of other medical care action candidates and said system is used for making a medical care schedule by determining at least two execution orders of a plurality of medical care action candidates which compose treatment procedure sequence candidates for treating a patient;

said method processes comprising:
- designating the plurality of medical care action candidates that compose the treatment procedure sequence candidates for treating the patient;
- designating a disease code and identifying a data set corresponding to the designated disease code;
- selecting a plurality of particular object files that include the medical care data indicating the designated plurality of medical care action candidates from among the plurality of object files set in advance;
- determining the at least two execution orders of the designated plurality of medical care action candidates in accordance with the position of execution of each of the designated plurality of medical care action candidates indicated by the setting order information of each of the selected plurality of particular object files and based on the plurality of object files included in the identified data set; and
- displaying the at least two execution orders of the designated plurality of medical care action candidates.

6. A system for aiding to make a medical care schedule by determining at least an execution order of a plurality of medical care actions which compose a treatment procedure sequence for a treatment of a particular patient, the system comprising:
- a plurality of object files set in advance, wherein the plurality of object files are divided into a plurality of data sets according to categories associated with patient attributes including at least a cardinal symptom, wherein each data set is assigned a different patient attribute code, each object file including:
  (i) medical care data indicating one of a plurality of medical care actions set in advance, and
  (ii) setting order information indicating at least a position of execution of one of the plurality of medical care actions in relation to the plurality of other medical care actions;
- an input device for designating the plurality of medical care actions which compose the treatment procedure sequence for the treatment of the particular patient, wherein the input device is adapted to designate a patient attribute code and to identify a data set corresponding to the designated patient attribute code;
- a process device for selecting a plurality of particular object files that respectively include the medical care data indicating the designated plurality of medical care actions from among the plurality of object files set in advance, and determining an execution order of the designated plurality of medical care actions in accordance with the position of execution of each of the designated plurality of medical care actions indicated by the setting order information of each of the selected plurality of particular object files and based on the plurality of object files included in the identified data set; and a display device for displaying the execution order of the designated plurality of medical care actions determined by the process device.

7. A system according to claim 6, wherein the process device determines, in addition to the execution order of the designated plurality of medical care actions, an execution timing of each of the designated plurality of medical care actions in accordance with the position of execution of each of the designated plurality of medical care actions indicated by the setting order information of each of the selected plurality of particular object files.

8. A system according to claim 7, wherein the input device is adapted to designate at least an execution date of at least one medical care action among the designated plurality of medical care actions, and the process device determines the execution date of each of the plurality of medical care actions based on the designated execution date.

9. A system according to claim 6, further comprising a memory device for storing a data set, which includes a plurality of object files corresponding to the designated plurality of medical care actions, in correlation with a patient code assigned to the particular patient, wherein the input device is adapted to designate the patient code and to identify the data set corresponding to the designated patient code, and the process device determines the execution order of the designated plurality of medical care actions based on the plurality of object files included in the identified data set.

10. A system according to claim 6, wherein the designated medical care actions are previously dedicated medical care actions, and the input device is adapted to change at least one of a designation of at least one of the plurality of previously designated medical care actions and a determination of at least one of the previously determined execution timings, the process device redetermines the execution order of the designated plurality of medical care actions when the execution timings are changed by the input device; and the display device displays the redetermined execution order of the designated plurality of medical care actions.

11. A system according to claim 10, wherein the process device transmits change-information data to the object file corresponding to at least one of the designated plurality of medical care actions when the execution timing of one of the designated plurality of medical care actions is changed.

12. A system according to claim 6, wherein the process device generates execution timing data indicating the execution timing of each of the designated plurality of medical care actions, and stores the execution timing data into the corresponding object files;

the process device determines the execution order of the designated plurality of medical care actions by using the stored execution timing data.

13. A system according to claim 6, wherein the display device displays the medical care data corresponding to the designated plurality of medical care actions.

14. A system according to claim 6, further comprising an alarm device for generating an alarm when the designated plurality of medical care actions contain at least two medical care actions whose positions of execution are in conflict.

15. A system according to claim 6, wherein the system comprises two units communicating with each other through a communication line, the plurality of object files are provided in one of the two units, and the display device is provided in the other of the two units.

16. A system according to claim 6, wherein the input device is adapted to change the setting order information.

17. A system according to claim 6, wherein the setting order information includes relational prescribing data, wherein the relational prescribing data prescribes a before and after relation between the position of execution of one of the plurality of medical care actions and the position of execution of at least another of the plurality of medical care actions.

18. A system according to claim 6, wherein the setting order information includes time range prescribing data which prescribes a range of a time period required for an execution of one of the plurality of medical care actions.

19. A system according to claim 6, wherein the setting order information includes execution frequency prescribing data which prescribes an execution frequency of one of the plurality of medical care actions.

20. A system according to claim 6, wherein the display device displays the medical care data corresponding to the designated plurality of medical care actions in a manner so that the medical care data corresponding to the designated plurality of medical care actions are arranged in the determined execution order.

21. A system according to claim 6, wherein the display device displays the medical care data corresponding to the designated plurality of medical care actions in a manner so that the medical care data corresponding to the designated plurality of medical care actions are arranged in a table so that time units indicating at least dates are set in one of two rows and at least types of medical care actions are set in the other of the two rows.

22. A system according to claim 21, wherein:

each of the plurality of object files includes multiple correlation information that indicates one or more relationships between each of the plurality of object files and at least one type of medical care action, and indicates a priority order of the relationship, and the process device correlates the plurality of object files with the types of medical care actions set in the other of the two rows in the table, based on the multiple correlation information.

23. A system according to claim 21, wherein the process device deletes the at least one type of medical care action set in the other of the two rows when the at least one type of medical care action has no corresponding object file.

24. A system according to claim 21, wherein the process device deletes at least one date set in said one of the two rows of the table when the at least one date has no corresponding object file.

25. A system for making a medical care schedule by generating at least two execution orders of a plurality of medical care action candidates, which compose treatment procedure sequence candidates for treating a patient, the system comprising:
- a plurality of object files set in advance, wherein the plurality of object files are divided into a plurality of data sets according to categories associated with patient attributes including at least a cardinal symptom, wherein each data set is assigned a different patient attribute code, each object file including:
  (i) medical care data indicating one of a plurality of medical care action candidates set in advance, and
  (ii) setting order information indicating at least a position of execution of said one of the plurality of medical care action candidates in relation to the plurality of other medical care action candidates;
- an input device for designating the plurality of medical care action candidates which compose the treatment procedure sequence candidates for treating the patients wherein the input device is adapted to designate the patient attribute code and to identify a data set corresponding to the designated patient attribute code;
- a process device for selecting a plurality of object files, each object file including the medical care data indicating the designated plurality of medical care action candidates from among the plurality of object files set in advance, and determining the at least two execution orders of the designated plurality of medical care action candidates in accordance with the position of execution of each of the designated plurality of medical care action candidates indicated by the setting order information of each of the selected plurality of particular object files and based on the plurality of object files included in the identified data set; and
- a display device for displaying the at least two execution orders of the designated plurality of medical care action candidates determined by the process device.

26. A system according to claim 25, wherein
the display device displays the at least two execution orders of the designated plurality of medical care action candidates in a manner such that the at least two execution orders of the designated plurality of medical care action candidates are arranged in a decision tree format.

27. A computer readable medium having a program of computer-readable instructions to be read by a system to perform method processes, said system comprising a plurality of object files, wherein the plurality of object files are divided into a plurality of data sets according to categories associated with patient attributes including at least a cardinal symptom, wherein each data set is assigned a different patient attribute code, each object file including (i) medical care data indicating one of various medical care actions set in advance, and (ii) setting order information indicating at least a position of execution of said one of the various medical care actions among the various medical care actions, said system is used for making a medical care schedule by determining at least an execution order of a plurality of medical care actions which compose a treatment procedure sequence for treating a patient, said method processes comprising:
- designating the plurality of medical care actions that compose the treatment procedure sequence for treating the patient;
- designating a patient attribute code and identifying a data set corresponding to the designated patient attribute code;
- selecting a plurality of particular object files that include the medical care data indicating the designated plurality of medical care actions from among the plurality of object files set in advance;
- determining the execution order of the designated plurality of medical care actions in accordance with the position of execution of each of the designated plurality of medical care actions indicated by the setting order information of each of the selected plurality of particular object files and based on the plurality of object files included in the identified data set; and
- displaying the execution order of the designated plurality of medical care actions.

28. A computer readable medium having a program of computer-readable instructions, to be read by a system to perform method processes, said system comprising: a plurality of object files, wherein the plurality of object files are divided into a plurality of data sets according to categories associated with patient attributes including at least a cardinal symptom, wherein each data set is assigned a different patient attribute code, each object file including (i) medical care data indicating one of a plurality of medical care action candidates set in advance, and (ii) setting order information indicating at least a position of execution of said one of the plurality of medical care action candidates among the plurality of other medical care action candidates and said system is used for making a medical care schedule by determining at least two execution orders of a plurality of medical care action candidates which compose treatment procedure sequence candidates for treating a patient;

said method processes comprising:
- designating the plurality of medical care action candidates that compose the treatment procedure sequence candidates for treating the patient;
- designating a patient attribute code and identifying a data set corresponding to the designated patient attribute code;
- selecting a plurality of particular object files that include the medical care data indicating the designated plurality of medical care action candidates from among the plurality of object files set in advance;
- determining the at least two execution orders of the designated plurality of medical care action candidates in accordance with the position of execution of each of the designated plurality of medical care action candidates indicated by the setting order information of each of the selected plurality of particular object files and based on the plurality of object files included in the identified data set; and
- displaying the at least two execution orders of the designated plurality of medical care action candidates.

* * * * *